(12) United States Patent
Britton et al.

(10) Patent No.: US 11,779,402 B2
(45) Date of Patent: *Oct. 10, 2023

(54) ROBOTIC SHOULDER REPAIR AND RECONSTRUCTION

(71) Applicant: MedTech S.A., Montpellier (FR)

(72) Inventors: Orsa Britton, Warsaw, IN (US); Pierre Couture, Montreal (CA)

(73) Assignee: MedTech S.A., Montpellier (FR)

( * ) Notice: Subject to any disclaimer, the term of this patent is extended or adjusted under 35 U.S.C. 154(b) by 272 days.

This patent is subject to a terminal disclaimer.

(21) Appl. No.: 17/218,455

(22) Filed: Mar. 31, 2021

(65) Prior Publication Data
US 2021/0236211 A1    Aug. 5, 2021

Related U.S. Application Data

(63) Continuation of application No. 16/210,787, filed on Dec. 5, 2018, now Pat. No. 10,987,175.
(Continued)

(51) Int. Cl.
*A61B 34/00* (2016.01)
*A61B 34/20* (2016.01)
(Continued)

(52) U.S. Cl.
CPC .............. *A61B 34/20* (2016.02); *A61B 34/30* (2016.02); *A61B 34/35* (2016.02); *A61B 34/70* (2016.02); *A61B 90/06* (2016.02); *A61B 90/50* (2016.02); *A61B 17/1684* (2013.01); *A61B 34/10* (2016.02); *A61B 34/32* (2016.02); *A61B 2034/105* (2016.02); *A61B 2034/107* (2016.02); *A61B 2034/108* (2016.02);
(Continued)

(58) Field of Classification Search
CPC ............ A61B 34/30; A61B 90/06; A61F 2/40
See application file for complete search history.

(56) References Cited

U.S. PATENT DOCUMENTS 2,752,116 A    6/1956  Minnis
3,910,538 A   10/1975  Baitella
(Continued)

FOREIGN PATENT DOCUMENTS

CN    107614817 A      1/2018
DE   102015104810 A1   9/2016
(Continued)

OTHER PUBLICATIONS

US 10,792,124 B2, 10/2020, Billard et al. (withdrawn)
(Continued)

*Primary Examiner* — Jason-Dennis N Stewart
(74) *Attorney, Agent, or Firm* — Schwegman Lundberg & Woessner, P.A.

(57) ABSTRACT

Methods and surgical system for performing a surgical procedure. The surgical system includes a robotic system with a robotic arm having a surgical instrument attached thereto. A computer system of the robotic system receives at least one image and forms a model of a surgical area. A computer operated tracking system of the robotic system obtains position data related to a patient's bone from tracking elements. Based on the model of the surgical area and the tracked bone position, the robotic arm then performs the surgical procedure with the surgical instrument, and the robotic system adjusts the procedure as a result of the tracked bone position.

18 Claims, 20 Drawing Sheets

Related U.S. Application Data

(60) Provisional application No. 62/688,749, filed on Jun. 22, 2018, provisional application No. 62/595,442, filed on Dec. 6, 2017.

(51) Int. Cl.

| | | |
|---|---|---|
| *A61B 90/00* | (2016.01) | |
| *A61B 90/50* | (2016.01) | |
| *A61B 34/35* | (2016.01) | |
| *A61B 34/30* | (2016.01) | |
| *A61B 34/10* | (2016.01) | |
| *A61B 17/16* | (2006.01) | |
| *A61F 2/46* | (2006.01) | |
| *A61B 34/32* | (2016.01) | |

(52) U.S. Cl.
CPC ............... *A61B 2034/2046* (2016.02); *A61B 2034/2055* (2016.02); *A61F 2002/4633* (2013.01)

(56) References Cited

U.S. PATENT DOCUMENTS

| | | | |
|---|---|---|---|
| 4,402,481 A | 9/1983 | Sasaki | |
| 4,514,117 A | 4/1985 | Scott | |
| 5,348,259 A | 9/1994 | Blanco et al. | |
| 5,779,209 A | 7/1998 | Rello | |
| 5,824,085 A | 10/1998 | Sahay et al. | |
| 5,899,425 A | 5/1999 | Corey Jr. et al. | |
| 6,467,362 B2 | 10/2002 | Erikson | |
| 6,575,653 B1 | 6/2003 | Kräuter | |
| 6,860,877 B1 | 3/2005 | Sanchez et al. | |
| 7,182,731 B2 | 2/2007 | Nguyen et al. | |
| 7,611,378 B1 | 11/2009 | Brekosky et al. | |
| 9,592,096 B2 | 3/2017 | Maillet et al. | |
| D878,585 S | 3/2020 | Garcia | |
| 10,687,792 B2 | 6/2020 | Garcia et al. | |
| 10,687,915 B2 | 6/2020 | Schlosser et al. | |
| 10,772,704 B2 | 9/2020 | Garcia et al. | |
| 10,786,264 B2 | 9/2020 | Chegini et al. | |
| 10,835,345 B2 | 11/2020 | Billard et al. | |
| D910,848 S | 2/2021 | Garcia | |
| 10,987,175 B2 | 4/2021 | Britton et al. | |
| 11,179,222 B2 | 11/2021 | Schlosser et al. | |
| 11,389,142 B2 | 7/2022 | Garcia et al. | |
| 2002/0017857 A1 | 2/2002 | Hashimoto et al. | |
| 2002/0074472 A1 | 6/2002 | Gaida et al. | |
| 2002/0117857 A1 | 8/2002 | Eckstein | |
| 2002/0177857 A1 | 11/2002 | Otsuka et al. | |
| 2002/0188293 A1 | 12/2002 | Manzo | |
| 2004/0172012 A1 | 9/2004 | Otsuka et al. | |
| 2008/0142658 A1 | 6/2008 | Jurja | |
| 2008/0164395 A1 | 7/2008 | Chang et al. | |
| 2010/0020002 A1 | 1/2010 | Van et al. | |
| 2010/0200002 A1 | 8/2010 | Orban, III et al. | |
| 2011/0290855 A1 | 12/2011 | Moore et al. | |
| 2011/0315843 A1 | 12/2011 | Hung | |
| 2012/0182134 A1 | 7/2012 | Doyle | |
| 2012/0265240 A1 | 10/2012 | Ganske et al. | |
| 2013/0187022 A1 | 7/2013 | Duportal et al. | |
| 2013/0292522 A1 | 11/2013 | Sears | |
| 2013/0299658 A1 | 11/2013 | Hung | |
| 2014/0343572 A1 | 11/2014 | Windolf et al. | |
| 2014/0379038 A1 | 12/2014 | Dogramadzi et al. | |
| 2015/0032215 A1 | 1/2015 | Slamin et al. | |
| 2015/0100066 A1 | 4/2015 | Kostrzewski et al. | |
| 2016/0081753 A1 | 3/2016 | Kostrzewski | |
| 2016/0151120 A1 | 6/2016 | Kostrzewski et al. | |
| 2016/0270780 A1 | 9/2016 | Hall et al. | |
| 2017/0340210 A1 | 11/2017 | Chuang | |
| 2017/0340389 A1 | 11/2017 | Otto et al. | |
| 2017/0360521 A1 | 12/2017 | Johnson | |
| 2018/0116758 A1 | 5/2018 | Schlosser et al. | |
| 2018/0256217 A1 | 9/2018 | Dekel et al. | |
| 2018/0360544 A1 | 12/2018 | Vanheule et al. | |
| 2019/0167356 A1 | 6/2019 | Britton et al. | |
| 2019/0274665 A1 | 9/2019 | Garcia | |
| 2019/0274777 A1 | 9/2019 | Garcia et al. | |
| 2019/0274778 A1 | 9/2019 | Billard et al. | |
| 2019/0274780 A1 | 9/2019 | Nowatschin et al. | |
| 2020/0281576 A1 | 9/2020 | Garcia et al. | |
| 2020/0352676 A1 | 11/2020 | Schlosser et al. | |

FOREIGN PATENT DOCUMENTS

| | | | |
|---|---|---|---|
| EP | 1327814 | A2 | 7/2003 |
| EP | 2777539 | A2 | 9/2014 |
| EP | 20143372 | B1 | 12/2014 |
| EP | 3274521 | A1 | 1/2018 |
| JP | S57144399 | A | 9/1982 |
| JP | 63280911 | A | 11/1988 |
| JP | S63280911 | A | 11/1988 |
| JP | 2001187064 | A | 7/2001 |
| JP | 2018509273 | A | 4/2018 |
| JP | 2021062232 | A | 4/2021 |
| WO | WO-9639944 | A1 | 12/1996 |
| WO | WO-2014108898 | A1 | 7/2014 |
| WO | WO-2016160272 | A1 | 10/2016 |
| WO | WO-2017017443 | A1 | 2/2017 |
| WO | WO-2017151887 | A1 | 9/2017 |
| WO | WO-2019177567 | A1 | 9/2019 |
| WO | WO-2019177569 | A1 | 9/2019 |
| WO | WO-2019177570 | A1 | 9/2019 |

OTHER PUBLICATIONS

"U.S. Appl. No. 16/877,023, Ex Parte Quayle Action mailed Apr. 29, 2021", 7 pgs.

"Canadian Application Serial No. 2,980,725, Office Action dated May 21, 2021", 6 pgs.

"European Application Serial No. 18713116.4, Response to Communication pursuant to Rules 161(1) and 162 EPC filed Apr. 29, 2021", 20 pgs.

"European Application Serial No. 18713548.8, Response to Communication pursuant to Rules 161(1) and 162 EPC filed Apr. 29, 2021", 21 pgs.

"European Application Serial No. 18713549.6, Response to Communication pursuant to Rules 161(1) and 162 EPC filed May 20, 2021", 23 pgs.

"Japanese Application Serial No. 2018-501138, Examiners Decision of Final Refusal dated May 11, 2021", (W/ English Translation), 6 pgs.

"Korean Application Serial No. 10-2017-7030940, Notice of Preliminary Rejection dated Feb. 4, 2021", (W/ English Translation), 4 pgs.

"Korean Application Serial No. 10-2017-7030940, Response filed Mar. 31, 2021 to Notice of Preliminary Rejection mailed Feb. 5, 2021", (W/English Translation), 11 pgs.

U.S. Appl. No. 15/560,894 U.S. Pat. No. 10/687,915, filed Sep. 22, 2017, Rapidly Repositionable Powered Support Arm.

U.S. Appl. No. 16/877,023, filed May 18, 2020, Rapidly Repositionable Powered Support Arm.

U.S. Appl. No. 16/210,787, filed Dec. 5, 2018, Robotic Shoulder Repair and Reconstruction.

U.S. Appl. No. 15/918,531 U.S. Pat. No. 10,687,792, filed Mar. 12, 2018, End Effector Coupler for Surgical Arm.

U.S. Appl. No. 29/640,121 U.S. Pat. No. D878,585, filed Mar. 12, 2018, End Effector Coupler Stem.

U.S. Appl. No. 29/721,682 U.S. Pat. No. D910,848, filed Jan. 22, 2020, End Effector Coupler Stem.

U.S. Appl. No. 16/879,500, filed May 20, 2020, End Effector Coupler for Surgical Arm.

U.S. Appl. No. 15/919,150 U.S. Pat. No. 10,772,704, filed Mar. 12, 2018, End Effector Coupler for Surgical Arm.

U.S. Appl. No. 16/994,181, filed Aug. 14, 2020, End Effector Coupler for Surgical Arm.

U.S. Appl. No. 17/015,734, filed Sep. 9, 2020, End Effector Coupler for Surgical Arm.

(56) References Cited

OTHER PUBLICATIONS

U.S. Appl. No. 15/919,161 U.S. Pat. No. 10/835,345, filed Mar. 12, 2018, End Effector Coupler for Surgical Arm.
"U.S. Appl. No. 16/877,023, Corrected Notice of Allowability dated Aug. 16, 2021", 2 pgs.
"U.S. Appl. No. 16/877,023, Notice of Allowance dated Jul. 22, 2021", 8 pgs.
"U.S. Appl. No. 16/877,023, Response filed Jun. 24, 2021 to Ex Parte Quayle Action mailed Apr. 29, 2021", 4 pgs.
"U.S. Appl. No. 16/879,500, Non Final Office Action dated Jan. 6, 2022", 11 pgs.
"U.S. Appl. No. 16/879,500, Notice of Allowance dated Mar. 21, 2022", 8 pgs.
"U.S. Appl. No. 16/879,500, Response filed Mar. 3, 2022 to Non Final Office Action dated Jan. 6, 2022", 8 pgs.
"Canadian Application Serial No. 2,980,725, Response filed Sep. 21, 2021 to Office Action dated May 21, 2021", 13 pages.
"European Application Serial No. 16773696.6, Communication Pursuant to Article 94(3) EPC dated May 30, 2022", 5 pgs.
"Japanese Application Serial No. 2018-501138, Response filed Sep. 13, 2021 to Examiners Decision of Final Refusal dated May 11, 2021", with English claims, 18 pages.
"3840 Series Holder", Fisso—Rail-mounted instrument holding arm / articulated, [Online]. [Accessed Oct. 16, 2017]. Retrieved from the Internet: <URL: http://www.medicalexpo.com/prod/fisso/product-67723-681104.html>, 3 pgs.
"3D-Arm™", Elekta—Minimally invasive surgery instrument holding arm, [Online]. [Accessed Oct. 16, 2017]. Retrieved from the Internet: <URL: http://www.medicalexpo.com/prod/elekta/product-70692-509376.html>, 8 pgs.
"ALLY Uterine Positioning System", Cooper Surgical, [Online]. [Accessed Oct. 16, 2017]. Retrieved from the Internet: <URL: https://www.coopersurgical.com/Products/Detail/ALLY-Uterine-Positioning-System>, 2 pgs.
"Anatomical Shoulder Fracture System", Zimmer Surgical Technique, 97-4223-003-00 Rev. 1, (2005), 24 pgs.
"Anatomical Shoulder Glenoid", Zimmer Surgical Technique, (2014), 12 pgs.
"U.S. Appl. No. 15/560,894, Final Office Action dated Nov. 29, 2019", 8 pgs.
"U.S. Appl. No. 15/560,894, Non Final Office Action dated May 16, 2019", 9 pgs.
"U.S. Appl. No. 15/560,894, Notice of Allowance dated Feb. 13, 2020", 8 pgs.
"U.S. Appl. No. 15/560,894, Preliminary Amendment filed Sep. 22, 2017", 7 pgs.
"U.S. Appl. No. 15/560,894, Response filed Jan. 28, 2020 to Final Office Action dated Nov. 29, 2019", 7 pgs.
"U.S. Appl. No. 15/560,894, Response filed Mar. 21, 2019 to Restriction Requirement dated Dec. 31, 2018", 9 pgs.
"U.S. Appl. No. 15/560,894, Response filed Aug. 16, 2019 to Non Final Office Action dated May 16, 2019", 11 pgs.
"U.S. Appl. No. 15/560,894, Restriction Requirement dated Dec. 31, 2018", 7 pgs.
"U.S. Appl. No. 15/560,894, Supplemental Preliminary Amendment filed Sep. 29, 2017", 7 pgs.
"U.S. Appl. No. 15/918,531, Corrected Notice of Allowability dated May 20, 2020", 2 pgs.
"U.S. Appl. No. 15/918,531, Non Final Office Action dated Sep. 26, 2019", 12 pgs.
"U.S. Appl. No. 15/918,531, Notice of Allowance dated Feb. 19, 2020", 11 pgs.
"U.S. Appl. No. 15/918,531, Response filed Dec. 26, 2019 to Non Final Office Action dated Sep. 26, 2019", 12 pgs.
"U.S. Appl. No. 15/919,150, Non Final Office Action dated Jan. 13, 2020", 10 pgs.
"U.S. Appl. No. 15/919,150, Notice of Allowance dated May 12, 2020", 5 pgs.
"U.S. Appl. No. 15/919,150, Response filed Apr. 10, 2020 to Non Final Office Action dated Jan. 13, 2020", 11 pgs.
"U.S. Appl. No. 15/919,150, Supplemental Notice of Allowability dated Jul. 6, 2020", 2 pgs.
"U.S. Appl. No. 15/919,150, Supplemental Notice of Allowability dated Jul. 29, 2020", 2 pgs.
"U.S. Appl. No. 15/919,161, Corrected Notice of Allowability dated Jul. 29, 2020", 2 pgs.
"U.S. Appl. No. 15/919,161, Corrected Notice of Allowability dated Aug. 26, 2020", 4 pgs.
"U.S. Appl. No. 15/919,161, Corrected Notice of Allowability dated Oct. 15, 2020", 2 pgs.
"U.S. Appl. No. 15/919,161, Final Office Action dated Feb. 19, 2020", 7 pgs.
"U.S. Appl. No. 15/919,161, Non Final Office Action dated Sep. 26, 2019", 18 pgs.
"U.S. Appl. No. 15/919,161, Notice of Allowance dated Jun. 4, 2020", 9 pgs.
"U.S. Appl. No. 15/919,161, Response filed May 18, 2020 to Final Office Action dated Feb. 19, 2020", 10 pgs.
"U.S. Appl. No. 15/919,161, Response filed Dec. 26, 2019 to Non Final Office Action dated Sep. 28, 2019", 13 pgs.
"U.S. Appl. No. 16/210,787, Non Final Office Action dated Sep. 15, 2020", 7 pgs.
"U.S. Appl. No. 16/210,787, Notice of Allowance dated Jan. 4, 2021", 8 pgs.
"U.S. Appl. No. 16/210,787, Response filed Jun. 15, 2020 to Restriction Requirement dated Apr. 16, 2020", 6 pgs.
"U.S. Appl. No. 16/210,787, Response filed Dec. 9, 2020 to Non Final Office Action dated Sep. 15, 2020", 8 pgs.
"U.S. Appl. No. 16/210,787, Restriction Requirement dated Apr. 16, 2020", 5 pgs.
"U.S. Appl. No. 16/877,023, Preliminary Amendment filed Jul. 31, 2020", 7 pgs.
"U.S. Appl. No. 16/877,023, Response filed Mar. 26, 2021 to Restriction Requirement dated Jan. 28, 2021", 10 pgs.
"U.S. Appl. No. 16/877,023, Restriction Requirement dated Jan. 26, 2021", 7 pgs.
"U.S. Appl. No. 16/879,500, Preliminary Amendment filed Jun. 19, 2020", 6 pgs.
"U.S. Appl. No. 29/640,121, Corrected Notice of Allowability dated Jan. 21, 2020", 4 pgs.
"U.S. Appl. No. 29/640,121, Notice of Allowance dated Nov. 5, 2019", 8 pgs.
"U.S. Appl. No. 29/721,682, Corrected Notice of Allowability dated Jan. 19, 2021", 3 pgs.
"U.S. Appl. No. 29/721,682, Examiner Interview Summary dated Sep. 17, 2020", 3 pgs.
"U.S. Appl. No. 29/721,682, Non Final Office Action dated Jun. 23, 2020", 7 pgs.
"U.S. Appl. No. 29/721,682, Notice of Allowance dated Oct. 5, 2020", 7 pgs.
"U.S. Appl. No. 29/721,682, Response filed Sep. 14, 2020 to Non Final Office Action dated Jun. 23, 2020", 9 pgs.
"ASSISTO Arm System", Geomed GMBH, [Online]. [Accessed Oct. 16, 2017]. Retrieved from the Internet: <URL: http://www.geomed.de/index.php?id=65&L=1>, 1 pg.
"Atlas™ Flex Arm System", Axcess Surgical, [Online]. [Accessed Oct. 16, 2017]. Retrieved from the Internet: <URL: http://www.axcesssurgical.com/axcess-surgical-innovations-products/atlas-flex-arm-system/>, 5 pgs.
"Atlas™ Rigid Arm System", Axcess Surgical, [Online]. [Accessed Oct. 16, 2017]. Retrieved from the Internet: <URL: http://www.axcesssurgical.com/axcess-surgical-innovations-products/atlas-rigid-arm-system/>, 6 pgs.
"Australian Application Serial No. 2016243292, First Examination Report dated Apr. 7, 2020", 4 pgs.
"Australian Application Serial No. 2016243292, Response filed Jun. 29, 2020 to First Examination Report dated Apr. 7, 20", 30 pgs.
"Australian Application Serial No. 2016243292, Response filed Sep. 30, 2020 to Subsequent Examiners Report dated Jul. 30, 2020", 30 pgs.
"Australian Application Serial No. 2016243292, Subsequent Examiners Report dated Jul. 30, 2020", 5 pgs.

(56) References Cited

OTHER PUBLICATIONS

"Australian Application Serial No. 2016243292, Subsequent Examiners Report dated Oct. 14, 2020", 3 pgs.

"Bookler® StrongArm™ Holder", Mediflex, [Online]. [Accessed Nov. 2, 2017]. Retrieved from the Internet: <URL: http://www.mediflex.com/product/bookler-strongarm-holder-and-positioner-set-12-30cm-post/>, (2015), 4 pgs.

"Canadian Application Serial No. 2,980,725, Office Action dated Nov. 12, 2020", 4 pgs.

"Canadian Application Serial No. 2,980,725, Response filed Mar. 11, 2021 to Office Action dated Nov. 12, 2020", 17 pgs.

"Canadian Application Serial No. 3,002,354, Office Action dated Apr. 27, 2020", 3 pgs.

"Canadian Application Serial No. 3,002,354, Office Action dated Jul. 4, 2019", 4 pgs.

"Canadian Application Serial No. 3,002,354, Response filed Aug. 4, 2020 to Office Action dated Apr. 27, 2020", 18 pgs.

"Canadian Application Serial No. 3,002,354, Response filed Dec. 20, 2019 to Office Action dated Jul. 4, 2019", 14 pgs.

"Chinese Application Serial No. 201680027778.9, Office Action dated Feb. 6, 2020", with English translation, 6 pages.

"Chinese Application Serial No. 201680027778.9, Office Action dated Jun. 12, 2020", with English translation, 18 pages.

"Chinese Application Serial No. 201680027778.9, Office Action dated Jul. 12, 2019", w/English Translation, 20 pgs.

"Chinese Application Serial No. 201680027778.9, Response filed Mar. 19, 2020 to Office Action dated Feb. 6, 2020", with English claims, 8 pages.

"Chinese Application Serial No. 201680027778.9, Response filed Jul. 15, 2020 to Office Action dated Jun. 12, 2020", with English claims, 71 pages.

"Chinese Application Serial No. 201680027778.9, Response filed Oct. 31, 2019 to Office Action dated Jul. 12, 2019", (w/English Claims), 15 pgs.

"Comprehensive Segmental Revision System, Proximal Humeral Reconstruction, Distal Humeral Reconstruction, Total Humeral Reconstruction", Zimmer Biomet Surgical Technique, 0097.1-US-en-REV0416, (2016), 68 pgs.

"EndoArm", Olympus, [Online]. [Accessed Nov. 2, 2017]. Retrieved from the Internet: <URL: https://www.olympus.co.jp/jp/news/2003b/nr030925endoj.html>, (Sep. 25, 2003), 4 pgs.

"EndoBoy", LUT—Pneumatic Arm, Grecco, 8 pgs.

"EndoCrane", Karl Storz—LEROY Retractors for Laparoscopic Colorectal Surgery, [Online]. [Accessed Oct. 16, 2017]. Retrieved from the Internet: <URL: https://www.karlstorz.com/cps/rde/xbcr/karlstorz_assets/ASSETS/2193800.pdf>, 16 pgs.

"European Application Serial No. 16773696.6, Extended European Search Report dated Nov. 19, 2018", 8 pgs.

"European Application Serial No. 16773696.6, Response filed Jun. 4, 2018 to Office Action dated Nov. 22, 2018".

"European Application Serial No. 16773696.6, Response filed Jun. 17, 2019 to Extended European Search Report dated Nov. 19, 2018", 18 pgs.

"European Application Serial No. 18210813.4, Extended European Search Report dated Apr. 12, 2019", 7 pgs.

"Genzyme Remote Surgical Retractor Arm Hands Free Pneumatic System", Renix International/Alibaba.com Copyright 1999-2017, [Online]. [Accessed Nov. 2, 2017]. Retrieved from the Internet: <URL: http://renix.trustpass.alibaba.com/product/50001078652-219532304/Genzyme_Remote_Surgical_Retractor_Arm_Hands_Free_Pneumatic_System.html>, 2 pgs.

"Helping Hand", Fraunhofer IPA—The helping hand in the operation room Research News, [Online]. [Accessed Oct. 16, 2017]. Retrieved from the Internet: <URL: https://www.fraunhofer.de/en/press/research-news/2015/november/helping-hand-in-the-operation-room.html>, (Nov. 2015), 2 pgs.

"International Application Serial No. PCT/US2016/021076, International Preliminary Report on Patentability dated Oct. 12, 2017", 11 pgs.

"International Application Serial No. PCT/US2016/021076, International Search Report dated Aug. 11, 2016", 4 pgs.

"International Application Serial No. PCT/US2016/021076, Invitation to Pay Add'l Fees and Partial Search Report dated May 25, 2016", 2 pgs.

"International Application Serial No. PCT/US2016/021076, Written Opinion dated Aug. 11, 2016", 8 pgs.

"International Application Serial No. PCT/US2018/021988, International Preliminary Report on Patentability dated Sep. 24, 2020", 8 pgs.

"International Application Serial No. PCT/US2018/021988, International Search Report dated Dec. 20, 2018", 4 pgs.

"International Application Serial No. PCT/US2018/021988, Written Opinion dated Dec. 20, 2018", 6 pgs.

"International Application Serial No. PCT/US2018/022004, International Preliminary Report on Patentability dated Sep. 24, 2020", 14 pgs.

"International Application Serial No. PCT/US2018/022004, International Search Report dated Feb. 14, 2019", 8 pgs.

"International Application Serial No. PCT/US2018/022004, Invitation to Pay Additional Fees dated Dec. 19, 2018", 15 pgs.

"International Application Serial No. PCT/US2018/022004, Written Opinion dated Feb. 14, 2019", 14 pgs.

"International Application Serial No. PCT/US2018/022006, International Preliminary Report on Patentability dated Sep. 24, 2020", 15 pgs.

"International Application Serial No. PCT/US2018/022006, International Search Report dated Feb. 8, 2019", 8 pgs.

"International Application Serial No. PCT/US2018/022006, Invitation to Pay Additional Fees dated Dec. 12, 2018", 16 pgs.

"International Application Serial No. PCT/US2018/022006, Written Opinion dated Feb. 8, 2019", 15 pgs.

"IronIntern", Automated Medical, [Online]. [Accessed Oct. 16, 2017]. Retrieved from the Internet: <URL: http://ironintern.com/iron-intern%E2%84%A2>, 1 pg.

"Japanese Application Serial No. 2018-501138, Final Notification of Reasons for Refusal dated Sep. 29, 2020", (W/ English Translation), 5 pgs.

"Japanese Application Serial No. 2018-501138, Notification of Reasons for Refusal dated Nov. 5, 2019", (w/English Translation), 15 pgs.

"Japanese Application Serial No. 2018-501138, Response filed Apr. 22, 2020 to Notification of Reasons for Refusal dated Nov. 5, 2019", with English claims, 15 pgs.

"Japanese Application Serial No. 2018-501138, Response filed Dec. 28, 2020 to Final Notification of Reasons for Refusal dated Sep. 29, 2020", (W/ English Claims), 11 pgs.

"Jarit Endoscope Holder", Integra, [Online]. [Accessed Oct. 16, 2017]. Retrieved from: <URL: https://www.integralife.com/endoscope-instrument-holder-set/product/surgical-instruments-hospitals-surgery-centers-tissue-banks-jarit-laparoscopic-endoscopes-endoscope-instrument-holder-set>, 18 pgs.

"Korean Application Serial No. 10-2017-7030940, Notice of Preliminary Rejection dated Aug. 10, 2020", (W/ English Translation), 13 pgs.

"Korean Application Serial No. 10-2017-7030940, Response filed Oct. 8, 2020 to Notice of Preliminary Rejection dated Aug. 10, 2020", (W/ English Translation), 34 pgs.

"M-Trac", Aesculap / B Braun, [Online]. [Accessed—Oct. 16, 2017]. Retrieved from the Internet: <URL: https://www.bbraun.com/en/products/b/m-trac.html>, 2 pgs.

"Martin's Arm", Hayden Medical (& others), [Online]. [Accessed Oct. 16, 2017]. Retrieved from the Internet: <URL: http://haydenmedical.com/surgical-retractors-martins-arm-retractors/>, 2 pgs.

"Mechanical Arm—Mod. 8470", Ansabere Surgical, [Online]. [Accessed Oct. 16, 2017]. Retrieved from the Internet: <URL: http://www.ansaberesurgical.com/en/productos/brazos-mecanicos/brazo-mecanico-mod-8470/>, 5 pgs.

"Phantom ML", TeDan Surgical Innovations, [Online]. [Accessed Nov. 14, 2017]. Retrieved from the Internet: <URL: http://www.tedansurgical.com/spine/articulating-arms/>, 2 pgs.

(56) References Cited

OTHER PUBLICATIONS

"Point Setter", Mitaka Kohki Co., Ltd. Operating / User's Manual Model: PSMS2, (Feb. 14, 2010), 28 pgs.

"PositionOR", Surgical Concept Designs, [Online]. [Accessed Nov. 14, 2017]. Retrieved from the Internet: <URL: http://surgical-concepts.com/products/PositionOR/>, 1 pg.

"Postioning Arm", Civco—Laparostat™ Kit, [Online]. [Accessed Oct. 16, 2017]. Retrieved from the Internet: <URL: http://www.civco.com/mmi/resources/ifu/043687.pdf>, 16 pgs.

"SaphLITE | RadLITE", Teleflex Medical, [Online]. [Accessed Nov. 14, 2017]. Retrieved from the Internet: <URL: https://www.teleflex.com/en/usa/prod_saphlite-radlite.php>, 1 pg.

"Saphlite/Saphlift", Genzyme Surgical Products (Jan. 7, 1999), [Online]. [Accessed Oct. 16, 2017]. Retrieved from the Internet: <URL: https://www.accessdata.fda.gov/cdrh_docs/pdf/K990062.pdf>, 5 pgs.

"Speed-Tract", Integra—Table Mounted Speed—Tract Retractor System, [Online]. [Accessedd Oct. 16, 2017]. Retrieved from the Internet: <URL: http://occ.integralife.com/products%2Fpdfs%2Fintegra%20table%20mounted%20speed-tract%20retractor%20system%20brochure.pdf>, 6 pgs.

"Spider2 Limb Positioner", Smith & Nephew, [Online]. [Accessed Nov. 14, 2017]. Retrieved from the Internet: <URL: http://www.smith-nephew.com/new-zealand/advanced-surgical-devices/key-products/sports-medicine/spider2-limb-positioner-for-shoulder--hip--knee--/>, 2 pgs.

"Spine Endoscope & Endoscope Holder", Maxer, [Online]. [Accessed Nov. 2, 2017]. Retrieved from the Internet: <URL: http://www.maxerendoscopy.com/index.php?option=com_content&view=article&id=190:spine-endoscope-endoscope-holder&catid=81:spine-endoscopy&Itemid=858>, (2013).

"SurgiAssist Camera Holder", SurgiToolsMIS, [Online]. [Acessed Nov. 14, 2017]. Retrieved from the Internet: <URL: https://www.surgitools.com/surgiassist-camera-holder.html>, 4 pgs.

"Synaptive BrightMatter Drive Robotic Surgical Video Arm System", Synaptive, [Online]. [Accessed Nov. 14, 2017]. Retrieved from the Internet: <URL: https://www.medgadget.com/2016/05/synaptive-brightmatter-drive-robotic-surgical-videoarm-system.html>, 3 pgs.

"TEE Transducer Holder", Civco, [Online]. [Accessed Oct. 16, 2017]. Retrieved from the Internet: <URL: http://www.civco.com/mmi/resources/product-support/TEE-Holder-Brochure_2008P-2339-Rev-2_low-res-8l9rv5.pdf>, 8 pgs.

"The Freehand System", Freehand—V1.2, [Online]. [Acessed Oct. 16, 2017]. Retrieved from the Internet: <URL: http://freehandsurgeon.com/Products/Detail?id=2>, 3 pgs.

"TiREX® Retractor System", Orion Surgical, [Online]. [Accessed Nov. 2, 2017]. Retrieved from the Internet: <URL: http://www.orion-surgical.com/english/tirex-retractor-system/components-of-the-tirex.html>, (2017), 2 pgs.

"Trimano 3D Support Arm", Maquet, [Online]. [Accessed Oct. 16, 2017]. Retrieved from the Internet: <URL: https://www.maquet.com/int/products/trimano-3d-support-arm/>, 3 pgs.

"UniARM Surgical Support System", Mitaka Kohki Co., Ltd. Operating / User Manual Version 1.1, [Online]. [Accessed Nov. 2, 2017]. Retrieved from the Internet: <URL: http://mitakausa.com/uniarm/>, (Mar. 20, 2009), 19 pgs.

"Unitrac Retraction & holding system for open & minimally invasive surgery", Aesculap Surgical Technologies—Surgical Instruments, (2010), 12 pgs.

"Unitrac® Pneumatic Holding Arm", Aesculap / B Braun, [Online]. [Accessed Oct. 16, 2017]. Retrieved from the Internet: <URL: https://www.bbraun.com/en/products/b/unitrac-pneumaticholdingarm.html>, 3 pgs.

"Vertek Articulating Arm", Medtronic—Copyright 2013, [Online]. [Accessed Nov. 2, 2017]. Retrieved from the Internet: <URL: http://global.medtronic.com/xg-en/healthcare-professionals/products/neurological/surgical-navigation-imaging/neurosurgery-imaging-surgical-navigation/surgical-procedures.html>, 2 pgs.

"Viky", Endocontrol Medical, [Online]. [Accessed 2014]. Retrieved from the Internet: <URL: http://www.endocontrol-medical.com/en/viky-en/>, 5 pgs.

"Wingman Scope Holder", Stryker, [Online]. [Accessed Nov. 14, 2017]. Retrieved from the Internet: <URL: http://www.stryker.com/cn/products/OREquipmentTelemedicine/EndoscopicSurgeryEquipment/Laparoscopy/Accessories/ScopeHolder/index.htm#>, 3 pgs.

ROBOTIC SHOULDER REPAIR AND RECONSTRUCTION

CLAIM OF PRIORITY

This application is a continuation of U.S. patent application Ser. No. 16/210,787, filed on Dec. 5, 2018, the benefit of priority of which is claimed hereby, and which is incorporated by reference herein in its entirety.

TECHNICAL FIELD

This document pertains generally, but not by way of limitation, to surgical systems that include robotic systems for the performance of medical surgical procedures. More particularly, this disclosure relates to, but not by way of limitation, automated robotic system assistance for use in shoulder arthroplasty and related surgical procedures.

BACKGROUND

Surgical procedures are exceptionally delicate and require significant skill by the surgeon performing the surgery. Typically, precision during surgery is paramount to ensure the best outcome possible for the patient. During surgical procedures, such as reaming a bone or placing an implant, precision is necessary for a successful surgery. Reaming too much bone, providing too much or too little tension on implants, misplacing implants, and the like can have serious health effects. These include need for follow up surgeries, loss of a range of motion, or failed implant equipment.

Surgical procedures related to joints in the body provide their own unique problems. For example, the shoulder joint is a complex joint with the scapula, clavicle and the humerus all coming together to enable a wide range of movement, at least in a properly functioning joint. In a properly functioning shoulder joint the head of the humerus fits into a shallow socket in the scapula, typically referred to as the glenoid. Articulation of the shoulder joint involves movement of the humeral head in the glenoid, with the structure of the mating surfaces and surrounding tissues providing a wide range of motion.

When the shoulder joint is damaged for any reason, including rheumatoid arthritis, osteoarthritis, rotator cuff arthroplasty, vascular necrosis, or bone fracture, repairing the damage can involve surgical procedures that require operations such as precise drilling of holes in the glenoid, reaming a cavity in the humerus, and inserting an implant into the cavity. Often, such procedures are done by surgeons using crude methods that include eyeballing measurements and attempting to account for patient movement by hand. Especially with limited visibility and the intricate nature of the shoulder, techniques to provide a surgeon with greater accuracy during shoulder repair or reconstruction would be beneficial to patient outcomes.

OVERVIEW

Many examples exist of difficulties related to surgical procedures where imprecision results in negative effects to the surgical result. In one example, during a shoulder procedure, when a guide pin is inserted into a glenoid, difficulties arise when significant damage to the glenoid is presented. Locating the precise location of the pin when significant deformities in the joint exists is problematic. When the guide pin is secured to the glenoid, locating the guide pin at the incorrect location and angle can have serious effects on the outcome of a surgery. Inserting the guide pin at the ideal location and orientation is further complicated by the tight operating space, poor visibility, and complex nature of the shoulder joint. Accordingly, the present inventors have determined that use of an image guided robotic arm could be beneficial in ensuring proper placement and alignment of a guide pin for glenoid repair.

As another example, when excavating bone through a burring process, the depth, location and angle of the burring needs to be extremely precise to ensure that excess bone is not removed. Removal of excess bone results in weakening of the joint or bone and can be detrimental to the patient. In shoulder reconstruction procedures, it is often necessary to replace the head of the humerus, which requires reaming out a portion of the proximal humerus to receive a stem of a humeral implant (prosthesis).

As a solution to these types of surgical procedure difficulties, jig devices are utilized. However, jig devices can be limited in the intraoperative adjustments to the surgical plan and can be prone to manufacturing errors. These errors result in reverting to a conventional shoulder procedure that requires cleaning off the labrum and other soft tissues to achieve mating with the jig device.

Additionally, some current methods of shoulder fracture surgery and repair are relatively primitive. As an example, with regard to fracture repair, in an initial step, a canal needs to be reamed into the humerus. As a result of patient movement, and need to use landmarks to determine proper depth of the ream, over reaming is common. Cement then must be used to fill in and correct the over reaming, weakening the bone and causing a potential loose fitting implant.

After the canal has been reamed as described above, a stem is placed in the humeral canal. This is done by hand or with the assistance of manual surgical instruments. Such manual surgical instruments can include a foam sleeve that can be placed around the stem in order to attempt to hold the stem in place. Still, significant give is provided in the sleeve causing movement in the stem. Alternatively, a nurse or assistant can attempt to hold the stem to ensure proper placement, but imprecisions remain. Even when a limb positioner is employed to hold the humeral bone in place, significant instability of the stem can occur during the surgery.

Repairing a fractured shoulder joint can involve implanting a prosthesis (e.g., stem) and attaching bone fragments to the prosthesis and/or intact portion of the involved bones. In a fracture reconstruction surgery, a surgeon often doesn't have enough hands to keep the stem stable and properly positioned while taking additional surgical steps such as adding the tuberosities (e.g., bone fragments) back to the humerus. Consequently, this is a procedure that requires significant surgeon skill to accurately perform. As the complexity of the fracture increases, the degree of difficulty for the surgeon only rises. These types of imprecisions during surgery lead to problems for the patient, including but not limited to, improper tensioning in the shoulder replacement assembly resulting in loss of movement, early failures in replacement equipment, and additional surgeries.

In order to overcome these types of difficulties related to joint repair and replacement surgeries the inventors provide the current surgical system. The surgical system can include a robotic system that receives images of a surgical area such as a joint or bone prior to surgery. The robotic system can utilize an autonomously or semi-autonomously controlled robotic arm and optionally one or more positionable surgical support arms. A computing system associated with the robotic system can create a virtual model of the surgical area from medical images for planning and execution of a surgical procedure. Based on the virtual model, one or more robotic arms of the robot can utilize surgical instruments to assist in performance of a surgical procedure. During the procedure, a computer operated tracking system associated with the robotic system receives position data form tracking elements that have been placed on bones of the joint of the patient. Based on this position data, the robotic system makes real-time adjustments in the surgical procedure to account for movement. As a result of using the robotic system to generate the model and adjust a procedure using the position data, positioning of implants can be improved, and unnecessary reaming or burring of bones is minimized (if not eliminated).

The robotic surgical system discussed herein can be programmed to operate autonomously, semi-autonomously, or through direct surgeon input. In any of the three modes of operation, the robotic surgical system can assist in precisely placing implants or performing operations in reference to anatomical structures. The robotic system can pre-operatively create virtual models of the target bones and/or joint. The virtual models can be used for pre-operative planning, which can produce instructions to direct operations of the robotic system during a surgical procedure. During the procedure, the robotic system can track reference markers on the target anatomical elements (e.g., bones and/or joints) to adjust planned implantations, resections, reaming, and other related operations to be performed by the robotic system.

This Overview is intended to provide non-limiting examples of the present subject matter—it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to devices, systems and methods for performing surgery on a surgical area such as a joint or individual bone. More specifically, the present application discusses a robotic surgical system for assisting in joint repair and/or reconstruction procedures. The Figures are all related to various examples of surgical procedures related to the shoulder joint, such as glenoid guide pin placement, shoulder fracture repair, burring, reaming, and the like, relating to shoulder arthroplasty or repair surgeries. While not shown, other examples using similar systems, devices and methodologies are contemplated. This includes, but is not limited to elbow replacement, thumb replacement, reverse shoulder replacement, rotator cuff arthroplasty, and the like.

Figure 1:
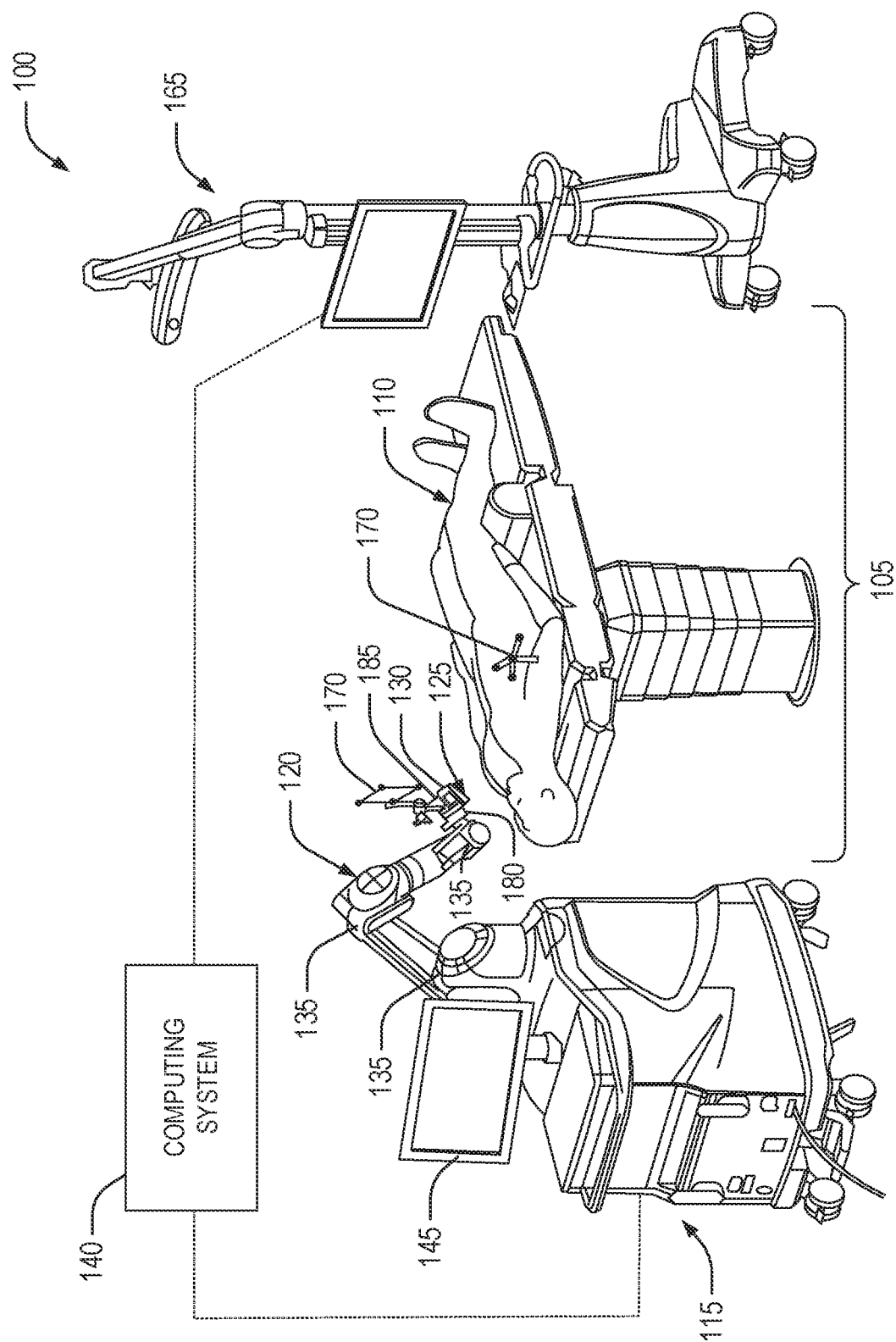
FIG. 1 illustrates a schematic diagram of a surgical system, in accordance with at least one example of the disclosure.
Figure 13:
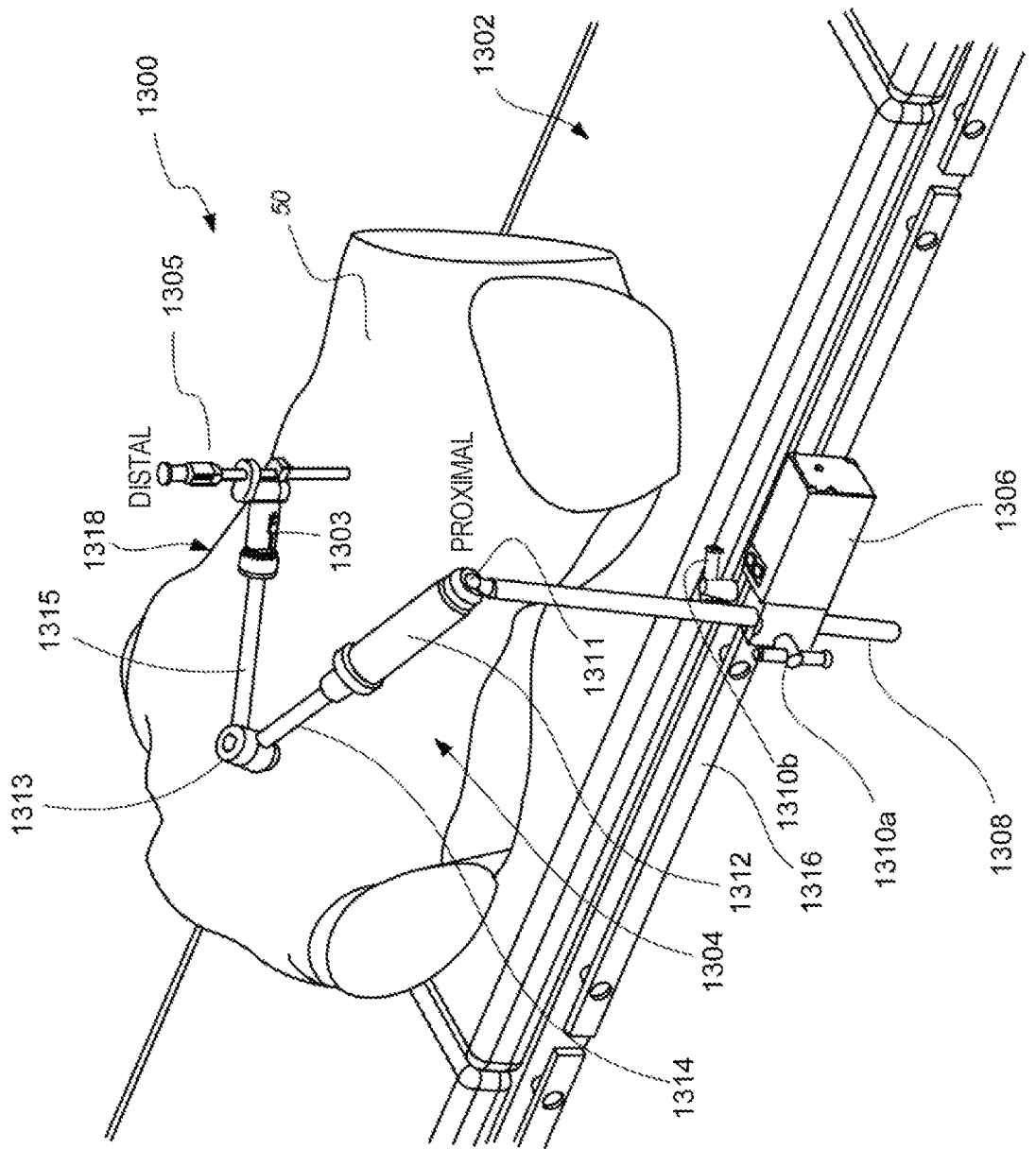
FIG. 13 illustrates a perspective view of a lockable surgical support arm, in accordance with at least one example of the disclosure.

FIG. 1 illustrates a surgical system 100 for operation on a surgical area 105 of a patient 110 in accordance with at least one example of the present disclosure. The surgical area 105 in one example can include a joint and in another example, is a bone. The surgical area 105 can include any surgical area of the patient 110, including but not limited to the shoulder, elbow, thumb, and the like. The surgical system 100 also includes a robotic system 115 with one or more robotic arms, such as robotic arm 120. As illustrated, the robotic system 115 will commonly utilize only a single robotic arm. The robotic arm 120 can be a 6 degree-of-freedom (DOF) robot arm, such as the ROSA robot from Medtech, a Zimmer Biomet Inc. company. In some examples, the robotic arm 120 is cooperatively controlled with surgeon input on the end effector or surgical instrument, such as surgical instrument 125 (also referred to herein as end effector 125). In other examples, the robotic arm 120 can operate autonomously. While not illustrated in FIG. 1, one or more positionable surgical support arms can be incorporated into the surgical system 100 to assist in positioning and stabilizing instruments or anatomy during a procedures. An example positionable surgical support arm is illustrated in FIG. 13 and discussed in detail below in reference to FIGS. 13-15B.

Each robotic arm 120 rotates axially and radially and receives a surgical instrument, or end effector, 125 at a distal end 130. The surgical instrument 125 can be any surgical instrument adapted for use by the robotic system 115, such as a gripping device such as a pincer grip, a burring device, a reaming device, an impactor device such as a humeral head impactor, or the like. The surgical instrument 125 is positionable by the robotic arm 120, which includes multiple robotic joints, such as joint 135, that allows the surgical instrument 125 to be positioned at any desired location adjacent or within a given surgical area 105.

The robotic system 115 also includes a computing system 140 that operates the robotic arms 120 and surgical instrument 125. The computing system 140 can include at least a memory, processing unit, and user input devices, as will be described herein. The computing system 140 also includes a human interface device 145 for providing images for a surgeon to be used during surgery. The computing system 140 is illustrated as a separate standalone system, but in some examples the computing system 140 can be integrated into the robotic system 115. The human interface device 145 provides images, including but not limited to three dimensional images of bones, glenoid, joints, and the like. The human interface device 145 can include associated input mechanisms, such as a touch screen, foot pedals, or other input devices compatible with a surgical environment.

The computing system 140 can receive pre-operative medial images. These images are received in any manner and the images include, but are not limited to computed tomography (CT) scans, magnetic resonance imaging (MRI), two dimensional x-rays, three dimensional x-rays, ultrasound, and the like. These images in one example are sent via a server as files attached to an email. In another example the images are stored on an external memory device such as a memory stick and coupled to a USB port of the robotic system to be uploaded into the processing unit. In yet other examples, the images are accessed over a network by the computing system 140 from a remote storage device or service.

After receiving one or more images, the computing system 140 can generate one or more virtual models related to surgical area 105. Specifically, a virtual model of the patient's anatomy can be created by defining anatomical points within the image(s) and/or by fitting a statistical anatomical model to the image data. The virtual model, along with virtual representations of implants, can be used for calculations related to the desired height, depth, inclination angle, or version angle of an implant, stem, surgical instrument, or the like related to be utilized in the surgical area 105. The virtual model can also be used to determine bone dimensions, implant dimensions, bone fragment dimensions, bone fragment arrangements, and the like. Any model generated, including three dimensional models, can be displayed on the human interface for reference during a surgery or used by the robotic system 115 to determine motions, actions, and operations of a robotic arm 120 or surgical instrument 125. Known techniques for creating virtual bone models can be utilized, such as those discussed in U.S. Pat. No. 9,675,461, titled "Deformable articulating templates" or U.S. Pat. No. 8,884,618, titled "Method of generating a patient-specific bone shell" both by Mohamed Rashwan Mahfouz, as well as other techniques known in the art.

The computing system 140 also communicates with a tracking system 165 that can be operated by the computing system 140 as a stand-alone unit. The surgical system 100 can utilize the Polaris optical tracking system from Northern Digital, Inc. of Waterloo, Ontario, Canada. The tracking system 165 can monitor a plurality of tracking elements, such as tracking elements 170, affixed to object of interest to track locations of multiple objects within the surgical field. The tracking system 165 functions to create a virtual three-dimensional coordinate system within the surgical field for tracking patient anatomy, surgical instruments, or portions of the robotic system 115. The tracking elements 170 can be tracking frames including multiple IR reflective tracking spheres, or similar optically tracked marker devices. In one example, the tracking elements are placed on or adjacent one or more bones of the patient 110. In other examples, the tracking elements 170 can be placed on a robot robotic arm 120, a surgical instrument 125, and/or an implant to accurately track positions within a virtual coordinate system. In each instance the tracking elements provide position data, such as patient position, bone position, joint position, robot robotic arm position, implant position, or the like.

The robotic system 115 can include various additional sensors and guide devices. For example, the robotic system 115 can include one or more force sensors, such as force sensor 180. The force sensor can provide additional force data or information to the computing system 140 of the robotic system 115. The force sensor 180 can be used to monitor impact or implantation forces during certain operations, such as insertion of an implant stem into a humeral canal. Monitoring forces can assist in preventing negative outcomes through force fitting components. In other examples, the force sensor 180 can provide information on soft-tissue tension in the tissues surrounding a target joint. In certain examples, the robotic system 115 can also include a laser pointer 185 that generates a laser beam or array that is used for alignment of implants during surgical procedures.

As discussed above, shoulder joint reconstruction can involve placement of a guide pin. One known technique for implanting a guide pin is a patient-specific instrument (PSI) jig or guide. However, PSI jigs do not easily allow for intraoperative adjustments to the surgical plan. PSI jigs can provide an opportunity for manufacturing errors in the PSI jigs to impact the surgical outcome, which may result in reverting to a conventional shoulder procedure. Additionally, PSI jigs can involve additional surgical operations, such as cleaning off the labrum and other soft tissues to achieve a good mating surface on the bone. Utilizing the surgical system 100 can allow for intraoperative adjustments to the surgical plan, as well as precise placement of the guide pin through use of the robotic arm.

Figure 2:
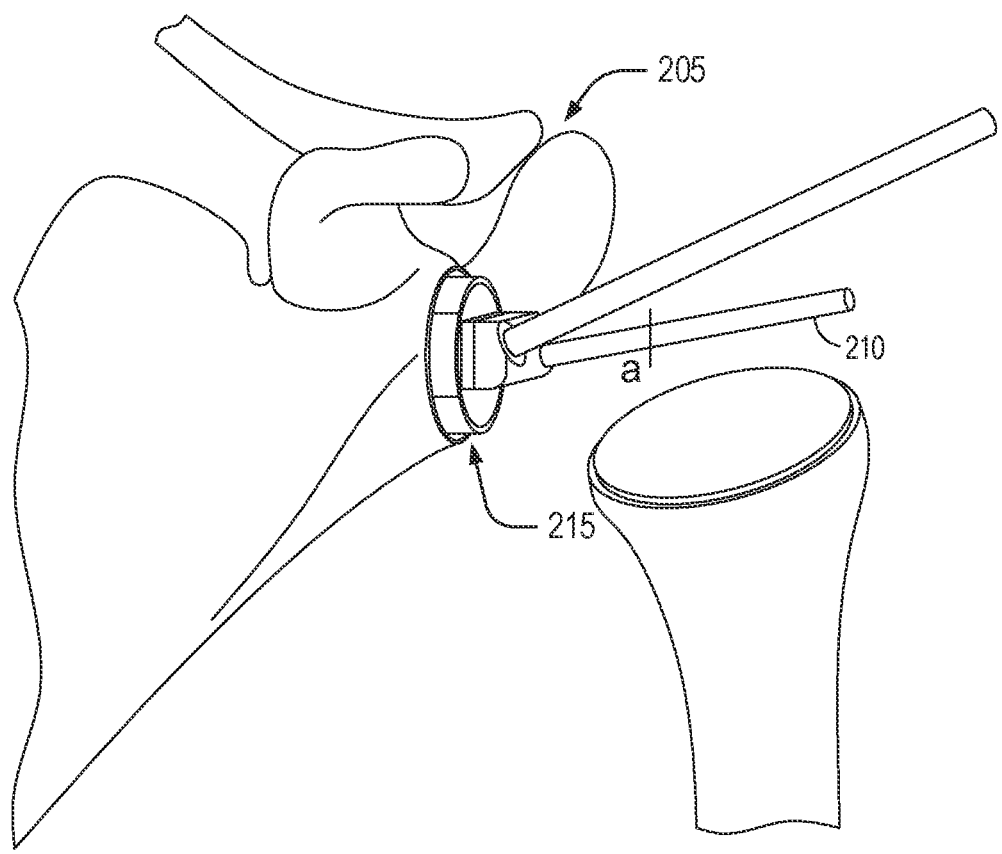
FIG. 2 illustrates a perspective view of a glenoid receiving a guide pin, in accordance with at least one example of the disclosure.
Figure 3:
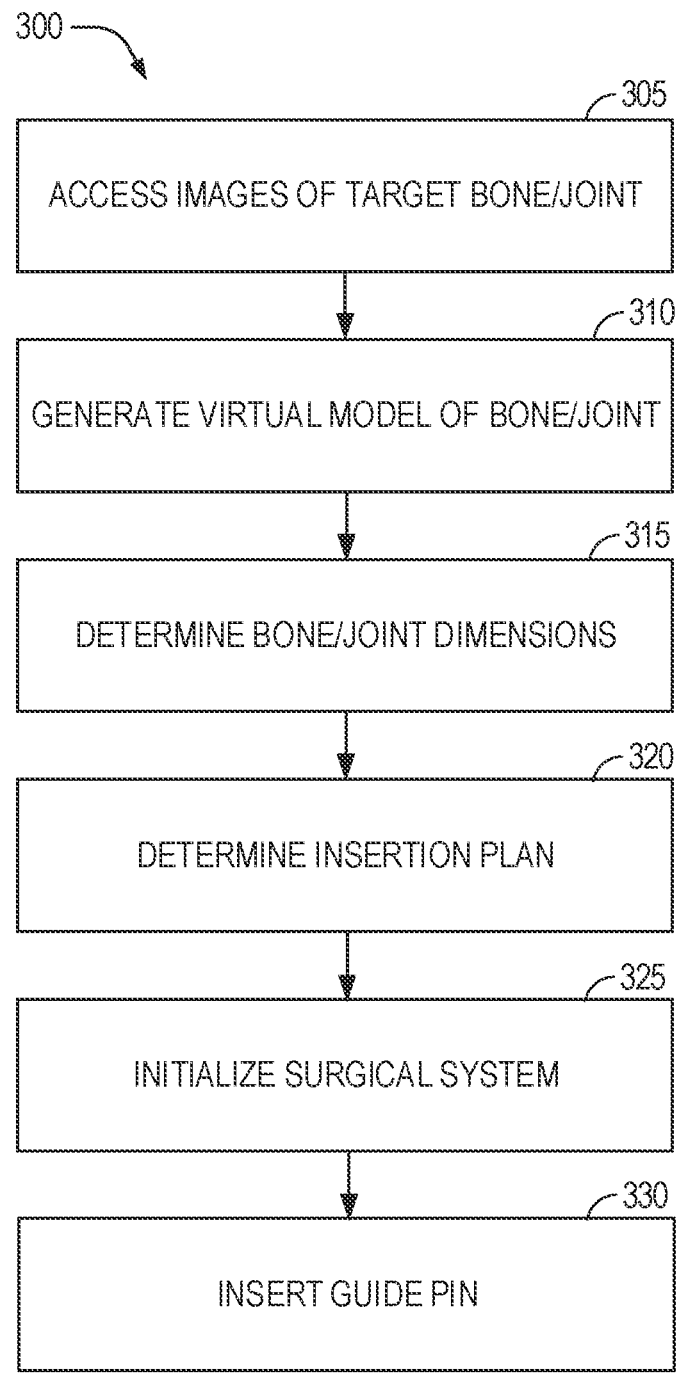
FIG. 3 illustrates a flow chart for a method of inserting a guide pin in a glenoid, in accordance with at least one example of the disclosure.

FIG. 2 illustrates an example of a joint repair utilizing the surgical system 100 of FIG. 1 to improve precision during a surgical procedure. In this example, the surgical procedure involves repair of a shoulder joint 205 including securing a guide pin 210 to the glenoid 215. As mentioned above, insertion of a glenoid guide pin, such as guide pin 210, is potentially critical to a positive outcome in certain shoulder arthroplasty procedures. Inserting the guide pin at the proper location and orientation (angle) can be challenging even when utilizing an insertion guide instrumentation FIG. 3 presents a flowchart outlining an example technique 300 to secure the guide pin 210 to the glenoid 215 using the example surgical system 100 presented in FIG. 1. In this example, the technique 300 can include operations such as: receiving medical images of a glenoid at 305, generating a glenoid virtual model at 310, determining glenoid dimensions at 315, determining guide pin insertion plan at 320, initializing the surgical system at 325, and inserting the guide pin at 330. The technique 300 can begin at 305 with images of the damaged glenoid being accessed by the computing system 140. At 310, the technique 300 continues with the computing system 140 of the surgical system 100 generating a virtual model of the glenoid, based on the image data accessed by the computing system 140. At 315, the technique 300 can continue with the computing system 140 determining the dimensions of the glenoid based on measurements performed on the virtual model of the glenoid. In an example, edge detection and other similar image processing techniques can be utilized to perform measurements on the virtual model. In other examples, the computing system 140 can present a user interface to a medical professional to allow virtual measurements to be made on the virtual model of the damaged glenoid. At 320, technique 300 can continue with the computing system 140 determining an insertion plan including location, depth, and angle in the glenoid for placement of the guide pin 210. In certain examples, the virtual model and glenoid measurements can be utilized by the computing system 140 to generate the insertion plan. In other examples, the computing system 140 can generate a user interface that allows the medical professional to plan insertion of the guide pin in the virtual glenoid, with the user interface providing visual and textual feedback regarding parameters relevant to guide pin insertion.

Once the insertion plan has been generated and is available for repair of the damaged shoulder, the surgical system 100 can be initialized for the procedure on the target patient. System initialization can include loading the insertion plan into computing system 140 and registering tracking markers affixed to necessary portions of the patient's anatomy and/or surgical instruments, among other things.

At 330, the technique 300 can proceed with the computing system 140 instructing the robotic system 115 to insert the guide pin according to the insertion plan. During operation 330, the computing system 140 receiving tracking information from the tracking system 165 to instruct the robotic system 115 in real-time to adjust the insertion plan based on tracked movements of the patient. Thus, the robotic system 115, based tracking information providing the glenoid position, inserts the guide pin into the planned position within the glenoid. During the insertion process 330, the robotic system 115 can autonomously insert the guide pin. In other embodiments, the robotic system 115 can be guided by a surgeon and provide feedback in accordance with the insertion plan to ensure the surgeon inserts the guide pin in the planned position and orientation. Guide pin insertion can include operations such as drilling a guide hole and then inserting the guide pin into the hole, or similar operations.

By using the procedure discussed in reference to FIG. 3, the exactness of the position of the guide pin is achieved without human error in placement of the guide pin. In addition, because the computing system 140 determines the exact location and angle of the guide pin (or allows the surgeon to pre-plan the location and angle), potential harm as a result of a misplaced guide pin is minimized. Further, at least in the examples where the robotic system 115 assists the surgeon, the experience and expertise of the surgeon is leveraged to ensure the planned insertion position and orientation are optimal. Therefore, the procedure of FIG. 3 utilizing the surgical system of FIG. 1 can deliver improved, consistent, and repeatable surgical results.

Figure 4:
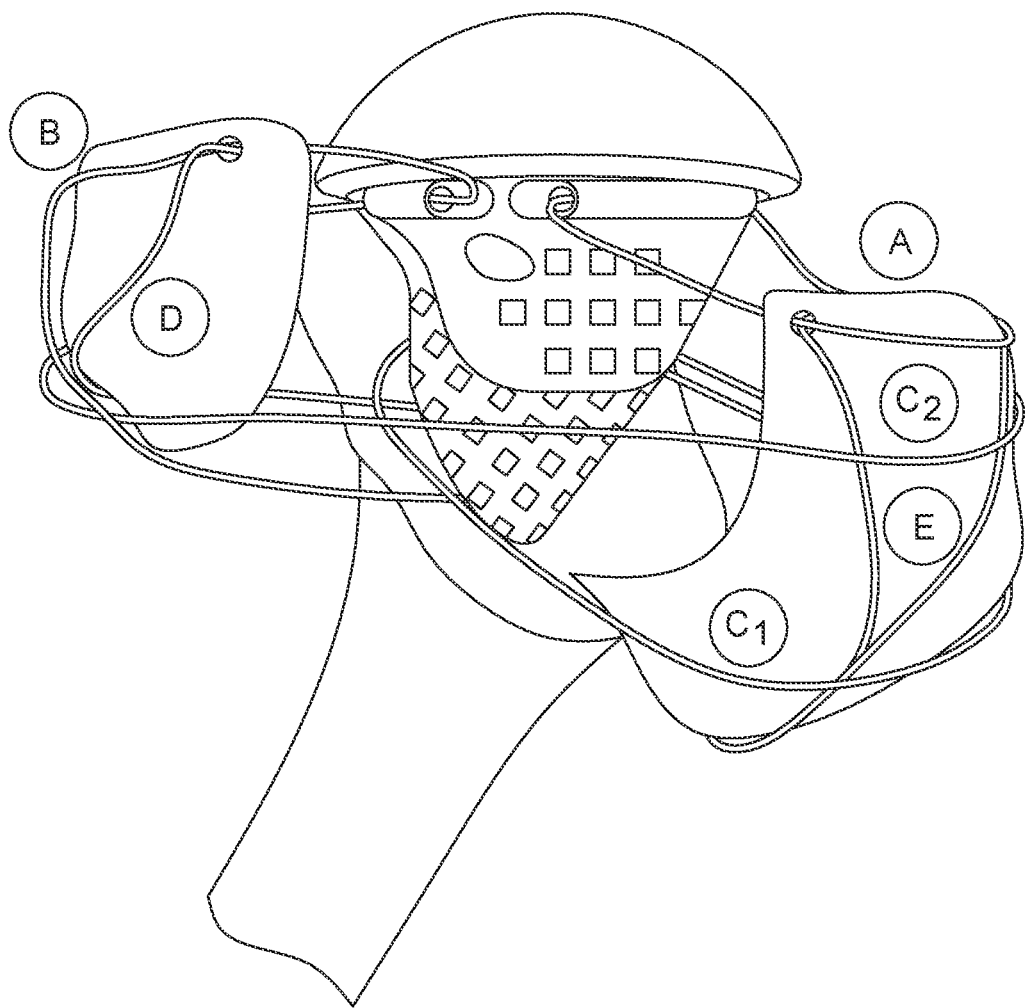
FIG. 4 illustrates a manual technique for humeral head fracture repair.
Figure 5A:
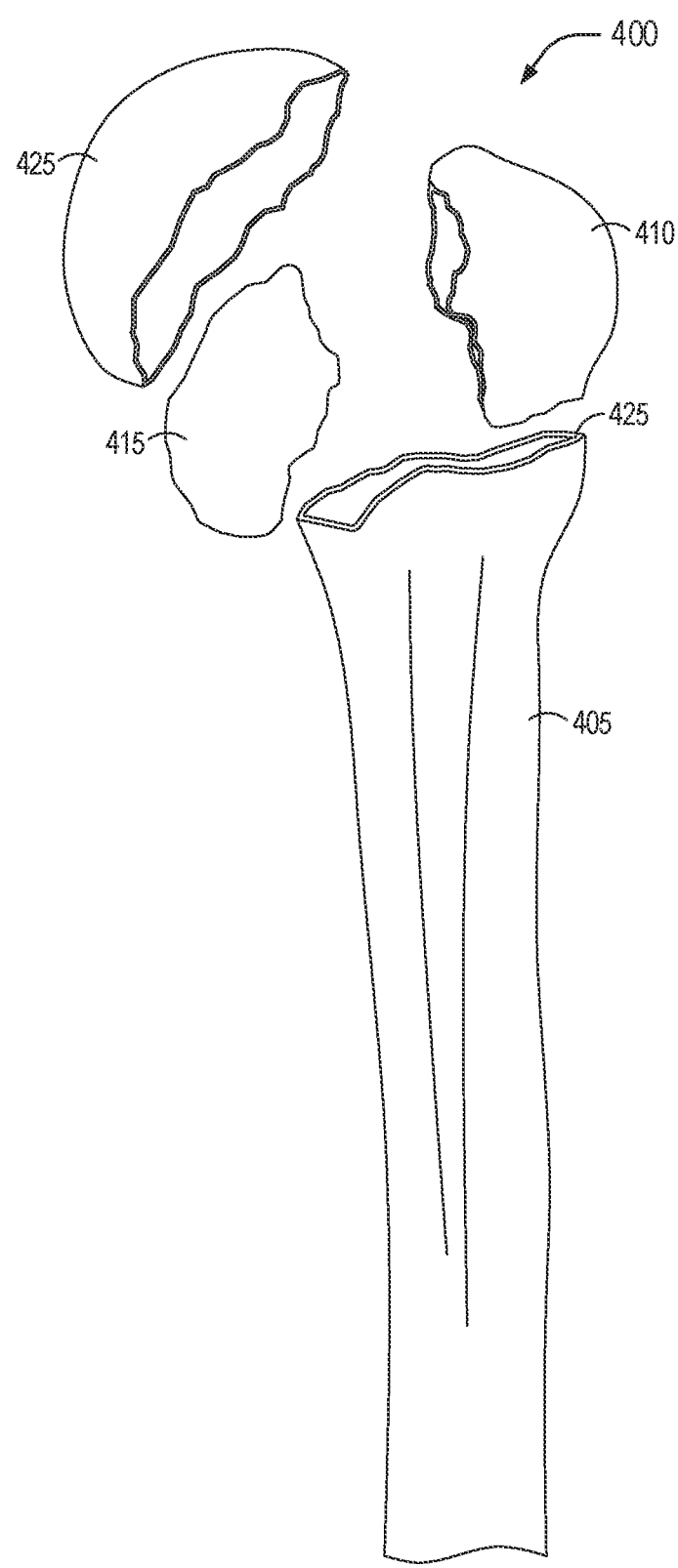
FIGS. 5A-5B illustrate a perspective views of a humeral bone multi part fracture, in accordance with at least one example of the disclosure.
Figure 5B:
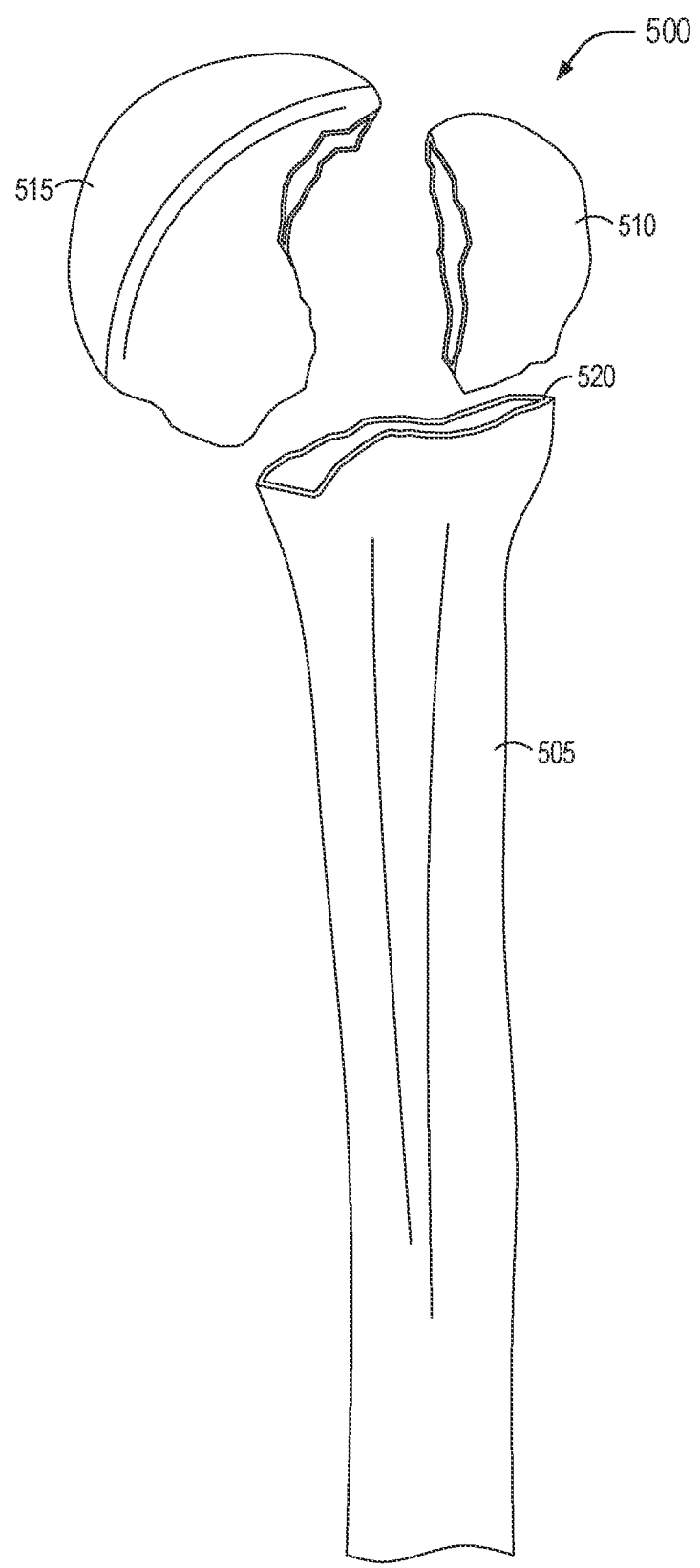

FIG. 4 illustrates a manual technique for humeral head fracture repair and FIGS. 5A-5B illustrate various humeral head fractures that can be repaired with assistance from the surgical system 100. As noted above, humeral head fractures can present numerous surgical challenges, including stabilizing a humeral implant while attending to reconstruction of the bone fragments (e.g., tuberosities). Repair of a humeral head fracture can involve insertion of a humeral implant and reattachment of the fracture fragments, often referred to as tuberosities. An example manual procedure is discussed in The Anatomical Shoulder™ Fracture System Surgical Technique from Zimmer Biomet, Inc. of Warsaw, IN. FIG. 4 includes a series of illustrations from the Zimmer Biomet surgical technique that highlight the complex nature of humeral head fracture repair. As shown in FIG. 4, repairing the fracture involves inserting and stabilizing an implant and then reattaching the various tuberosities with various complex sutures (see sutures A, B, $C_1$, $C_2$, D and E).

In this example, the surgical system 100 of FIG. 1 can be used to improve precision in surgery related to fracture repair surgery. FIGS. 5A and 5B show examples of humeral fractures. FIG. 5A shows a four-part fracture where a humeral bone 400 is fractured into four separate bone fragments 405, 410, 415, 420. The fractured humeral bone 400 includes a humeral shaft 405 with a fracture at a proximal end 425 where a greater tuberosity 410 and lesser tuberosity 415 fracture from the humeral shaft 405 and humeral head 420. In FIG. 5B a three-part fracture is provided where the fracture results in three separate bone fragments 505, 510, 515. In FIG. 5B the humeral bone 500 has a humeral shaft 505 with a fracture at a proximal end 520 that includes a greater tuberosity 510 and a lesser tuberosity 515. In this fracture a humeral head with a lesser tuberosity 515 is provided as a single bone fragment. While FIGS. 5A and 5B show three part and four part fractures, these are merely examples of fractures, the system is not necessarily limited to certain fracture types. The techniques and procedures discussed below involving the surgical system 100 in fracture repair are discussed, for purposed of example only, as operating on fractures with one greater tuberosity and one lesser tuberosity. However, the procedures can be adapted to fractures with more or fewer tuberosities involved in the fracture.

In a first example, the procedure for repairing a humeral head fracture utilizing the surgical system 100 involves using the robotic system 115 to prepare the humerus, implant the stem of the humeral prosthesis, and stabilize the humeral prosthesis while the surgeon reconnects the tuberosities. In this example, the robotic system 115 can maintain prosthesis position and orientation, which can include depth of insertion into the humerus, inclination angle and version angle. This example, leverages the skill and dexterity of the surgeon and various strengths of the robotic system 115, such as the ability to track and maintain relative position between the humerus and the humeral prosthesis throughout the procedure. In this example, the robotic system 115 can stabilize the prosthesis while bone cement is applied and/or after application of bone cement to allow curing of the bone cement to cement the stem into the humerus.

In a second example, the procedure for repairing a humeral head fracture utilizing the surgical system 100 involves the robotic system 115 performing or assisting in performance of all steps of the procedure. In this example, the procedure can be broken into various sub-procedures, including: pre operative planning, humeral implant preparation and implantation, and tuberosity reattachment of the tuberosities. Optionally, in this example, the surgeon may assist with reattachment of the tuberosities by performing the suturing or similar functions, while the tuberosity is held in position by the robotic system 115. In this example, image processing algorithms may be utilized to identify and map the tuberosities as well as suggest positions for reattachment of the tuberosities.

Figure 6:
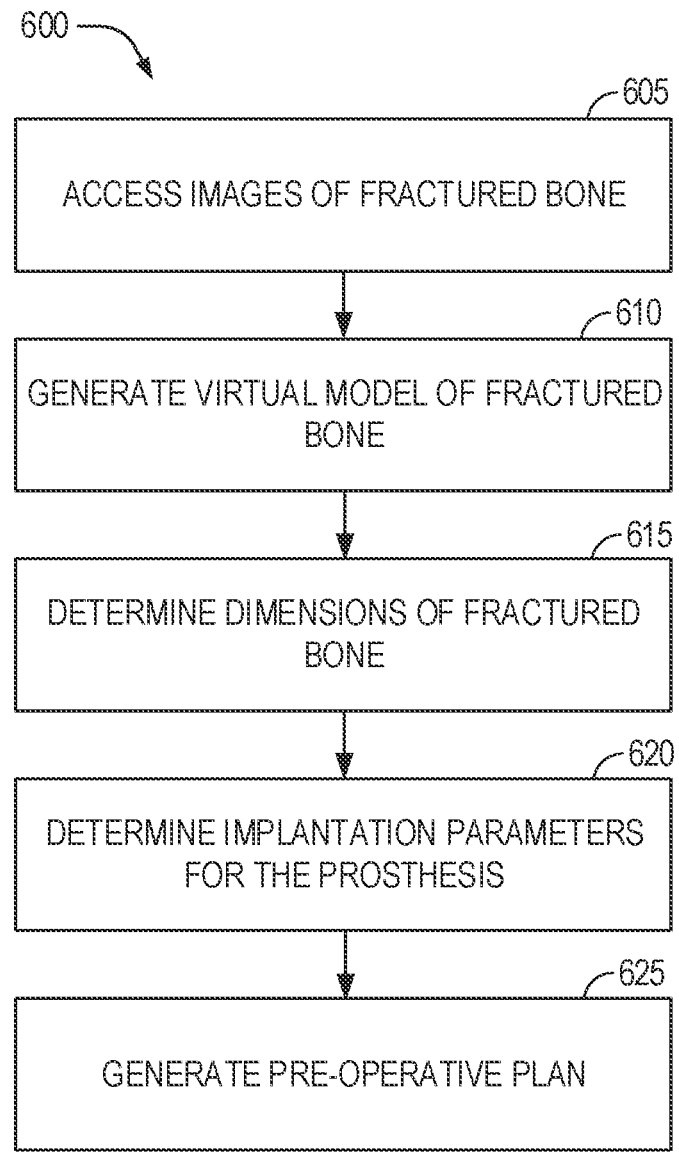
FIG. 6 is a flowchart illustrating a technique for pre-operative planning for a robotically assisted fracture repair procedure, in accordance with at least one example of the disclosure.

FIG. 6 is a flowchart illustrating a technique 600 for pre-operative planning for a robotically assisted fracture repair procedure, according to an example embodiment. The technique 600 can include operations such as: accessing medical images of the fractured bone at 605, generating a virtual model of the fracture bone at 610, determining dimensions of the fractured bone at 615, determining implant parameters at 620, and generating a pre-operative plan at 625. Both of the example fracture repair examples introduced above can utilize this pre operative planning technique to prepare a fracture repair plan.

The technique 600 can begin at 605, with the computing system 140 accessing medical images of fractured bone, such as fractured humerus 400 or 500. The medical images can be MRI, CT, or x-rays image data. The image data accessed at 605 can include the fracture fragments. At 610, the computing system 140 of the robotic system 115 can create a virtual model of the fractured humeral shaft based on at least one received image. In certain examples, the computing system 140 can also generate virtual models for each of the fracture fragments. The virtual models can be created through computerized analysis of the medical images, such as edge detection, blob analysis, surface fitting, and similar image processing techniques to generate virtual approximations of the fragments. Planning for fracture repair can include utilizing image data from the patient's healthy shoulder to assist in generating a desired outcome model for the fracture repair. The healthy shoulder model can be utilized to assist the computing system 140 in determining how best to reassemble the tuberosities to best reform the humerus of the damaged shoulder. The computing system 140 can also analyze the various bone fragments to suggest a reassembly plan for the fragments.

At 615, the technique 600 can continue with the computing system 140 determining dimensions of the fractured humeral shaft from the model. In certain examples, operation 615 can include generating a user interface for presentation to the surgeon to confirm the determined dimensions. At 620, the technique 600 can continue with the computing system 140 determining implantation parameters for implanting the prosthesis. In the shoulder joint fracture repair examples, the parameters for the humeral implant stem can include the location, angle (inclination and version) and depth of a cavity to ream within the humeral shaft. The implant parameters can also include determination of insertion depth, inclination, and version of the actual humeral implant after the cavity is reamed in the humeral shaft. The parameters need to account for the fracture at the proximal end of the humeral shaft, which can be determined and accounted for based on the virtual model.

The technique 600 can conclude at 625 with the computing system 140 generating a pre-operative plan. The pre-operative plan can include instructions to guide the robotic system 115 in performing or assisting with the fracture repair.

Figure 7A:
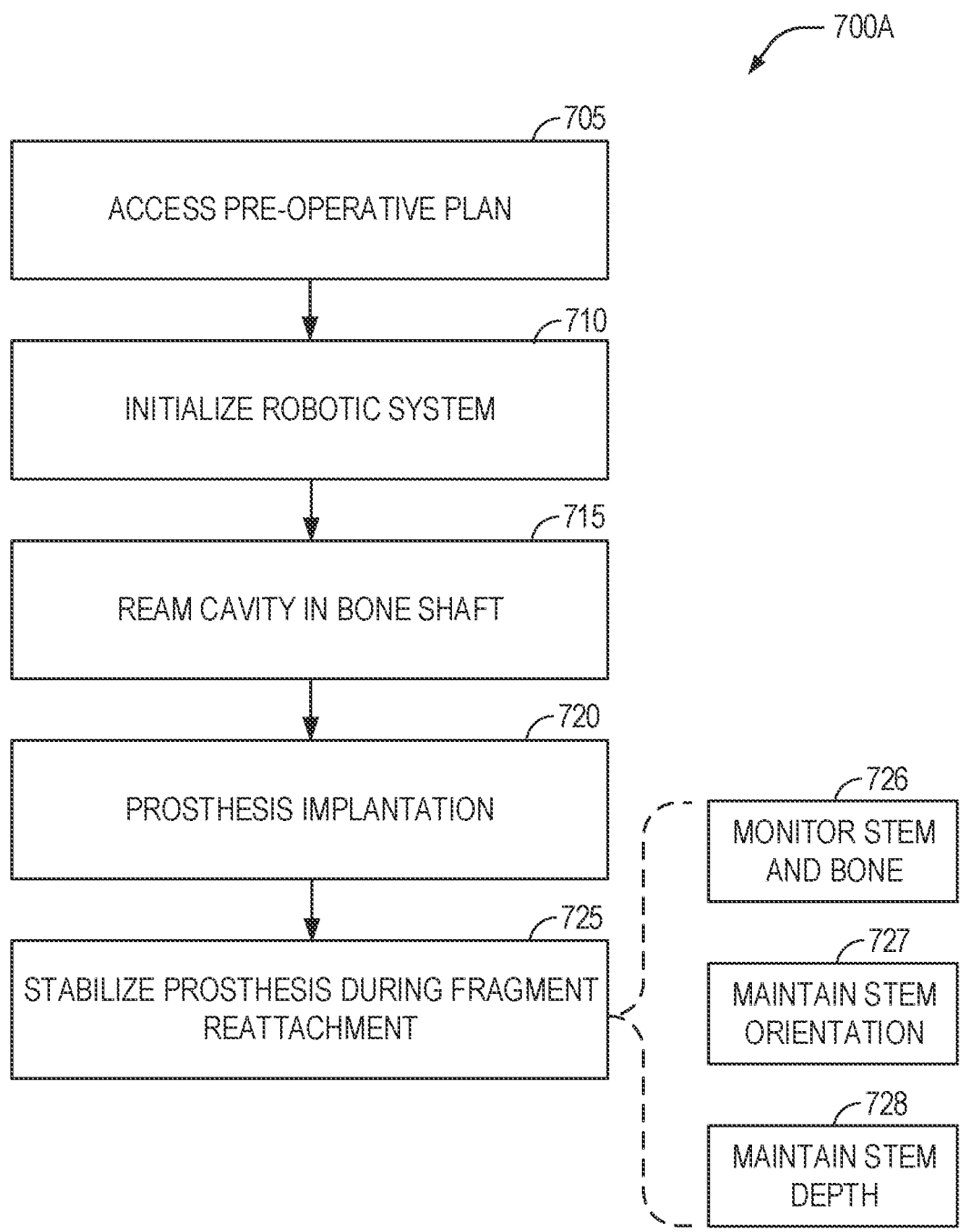
FIGS. 7A-7B are flowcharts illustrating robotically assisted fracture repair techniques, in accordance with at least one example of the disclosure.

FIG. 7A is a flowchart illustrating a robotically assisted fracture repair technique 700A, according to an example embodiment. Technique 700A illustrates a method utilizing the robotic system 115 to assist the surgeon in performing fracture repair. In this example, the robotic system 115 facilitates inserting the prosthesis and maintaining position of the prosthesis while the surgeon reattaches the fracture fragments (e.g., tuberosities). The technique 700A can include operations such as: accessing the pre-operative plan at 705, initializing the robotic system at 710, reaming a cavity in the humeral shaft at 715, implanting the prosthesis at 720, and stabilizing the prosthesis at 725.

The technique 700A can begin at 705 with the computing system 140 executing instructions to access a pre-operative plan, such as a pre-operative plan generated with technique 600. At 710, the technique 700A can continue with the computer system 140 operating to initialize the robotic system 115. Initializing the robotic system 115 can include coordination with the optical tracking system 165, to general a virtual coordinate system for the surgical field. Operation 710 can also include operations such as: registering the robotic arm 120 within a virtual coordinate system; registering the virtual model from the pre-operative plan to the physical anatomy including coordinating landmark locations on the physical anatomy to the virtual model; and displaying a user interface to guide the surgeon through the planned operation, among other things.

At 715, the technique 700A can continue with the robotic system 115 performing a reaming operation to create a cavity in the humeral shaft to receive the planned prosthesis. The reaming operation can be performed autonomously with the robotic system 115 and tracking system 165 working in coordination to track the target bone and guide the reaming instrument to generate the planned cavity. In other examples, the surgeon can guide the robotic arm 120 through manipulation of a reaming instrument attached to the end effector 125. In this example, the robotic system 115 can limit movements of the robotic arm 120 to prevent the surgeon from deviating from the planned resection. Throughout the cooperative control of the reaming instrument, the robotic system 115 can provide the surgeon opportunities to adjust the resection plan based on the surgeon's experience and ability to react to actual condition of the bone. The robotic system 115 can provide input mechanisms, such as a touch screen, foot pedals or buttons on the reaming instrument that can allow the surgeon an opportunity to override, in a limited fashion, safety boundaries enforced by the robotic system 115 based on the pre operative plan. As an additional safety measure, the override capabilities can be programmed to limit movement or resection outside the plan to a predetermined amount (angle variation, distance variation, etc. . . . ).

Once the cavity is reamed, the technique 700A can continue at 720 with the robotic system 115 performing prosthesis implantation into the reamed cavity. The pre-operative plan provides implant parameters, such as depth into the cavity in the target bone, inclination, and version. Ideally, the cavity is reamed in such a manner through robotic control that depth, inclination, and version are largely dictated by the cavity. However, in some examples, the cavity will allow for some adjustment in these parameters in implant insertion. Again, the prosthesis stem insertion can be performed autonomously by the robotic system 115 or cooperatively with the surgeon guiding movements of the robotic arm 120. In certain examples, securing the humeral stem in the reamed cavity may require use of bone cement. In these examples, the robotic arm 120 can stabilize the humeral stem while the bone cement cures sufficiently to stabilize the implant.

At 725, the technique 700A continues with the robotic system 115 and tracking system 165 operating to stabilize the prosthesis and maintain the planned position and orientation (e.g., depth, inclination, and version) while the surgeon reattaches the tuberosities. As illustrated, operation 725 can include the tracking system 165 monitoring the prosthesis and target bone. Monitoring can be done, in an example, by affixing tracking elements 170 to each of the prosthesis and the target bone. In certain embodiments, a tracking element 170 will only be affixed to the end effect 125 of the robotic arm 120 to closely monitor location of the prosthesis as it is held in place by an instrument attached to the end effector 125. In yet another example, the robotic arm 120 can include sensors that allow for the robotic system 115 to know the precise location of the robotic arm 120 and end effector 125, which can remove the need to a tracking element 170 to be affixed to the robotic arm 120 or the prosthesis during this operation. Operation 725 can also include maintaining prosthesis stem orientation (e.g., inclination and version) throughout this portion of the technique 700A. While the surgeon is working to reattach the tuberosities, slight movement of the humerus may occur, and the robotic system 115 can compensation for these movements through information provided by the tracking system 165. Finally, operation 725 can include maintaining prosthesis stem depth within the cavity in the target bone (e.g., humerus). In some examples, the stem of the prosthesis can include markings that assist the surgeon in visually verifying that the robotic system 115 is maintaining proper depth and orientation. In other examples, the surgeon may utilize a marking instrument to mark the depth and/or orientation to allow for visual monitoring during the procedure.

Figure 7B:
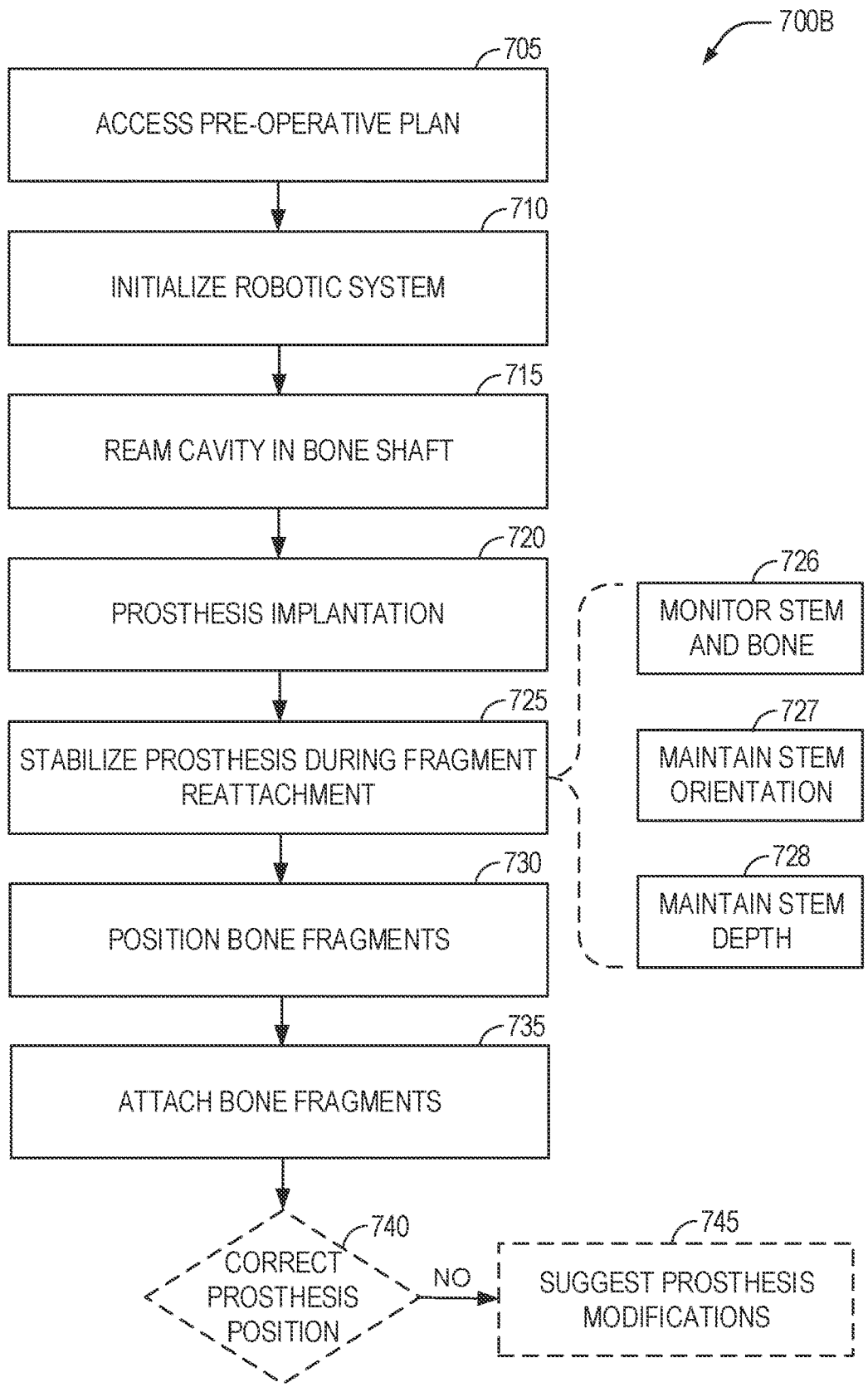

FIG. 7B is a flowchart illustrating a robotically assisted fracture repair technique 700B, according to an example embodiment. Technique 700B illustrates a method where the robotic system 115 performs the fracture repair under supervision by the surgeon. In this example, the robotic system 115 is adapted to reassemble the tuberosities like a jigsaw puzzle. The initial operations of technique 700B are essentially the same as the operations discussed above in reference to technique 700A. Operation 725 may deviate from the discussion above, as the robotic system 115 may optionally not continue to retain the prosthesis during the reattachment process, but will at a minimum continue to monitor the prosthesis location and orientation with reference to the target bone.

The unique aspects of technique 700B really being at operation 730, where the robotic system 115 operates to position bone fragments (e.g., tuberosities) around the prosthesis to affect the repair. In this example, the pre-operative plan can include virtual models of the major tuberosities, those of sufficient size to allow for robotic reattachment. The virtual models of the tuberosities can be used by the robotic system 115 to identify, locate, and grasp the tuberosity during operation 730. In some examples, the robotic system 115 may include additional hardware devices to assist with this task, such as special forceps or tweezers mounted on the end effector 125 that are specially designed to enable the robotic arm 120 to grasp the tuberosities. In another example, the robotic system 115 may include a small suction-cup type instrument mounted on the end effector 125 to grasp and position the tuberosities. Further, the robotic system 115 may include a stereo-optic visual tracking device mounted near the end effect to provide the robotic system 115 with the ability to identify and track the tuberosities within the surgical field. The robotic system 115 can utilize object recognition algorithms to identify the various tuberosities, the prosthesis, and the fractured bone in order to calculate the necessary trajectories to grasp and manipulate the individual tuberosities into the planned position.

At 735, the technique 700B can continue with the robotic system 115 reattaching the properly positioned tuberosities to the prosthesis and/or the fractured bone. The technique 700B may involve multiple iterations of operations 730 and 735 to address each of the tuberosities to be reattached during the procedure. The reattachment process can involve suturing the tuberosity to the prosthesis and/or the fractured bone. In an example, the robotic system 115 can be adapted to autonomously perform the suturing process. In other examples, the robotic system 115 can operation to hold the tuberosity in position while the surgeon sutures it into place. Technique 700B can benefit from a robotic system with multiple robotic arms 120, which would allow for holding and suturing with separate robotic arms, for example, At 740, the technique 700B can continue with the computing system 140 accessing tracking data from the tracking system 165 and/or the robotic system 115 to verify that the prosthesis has been maintained in an optimal position throughout the reattachment process. If the system determines that the prosthesis has not maintained an optimal position, the technique 700B can continue at 745 with the computing system 140 determining recommended prosthesis modifications to account for the sub-optimal positioning. For example, the prosthesis system may include various head and/or neck modules that can be substituted to account for the actual position of the prosthetic stem.

Figure 8A:
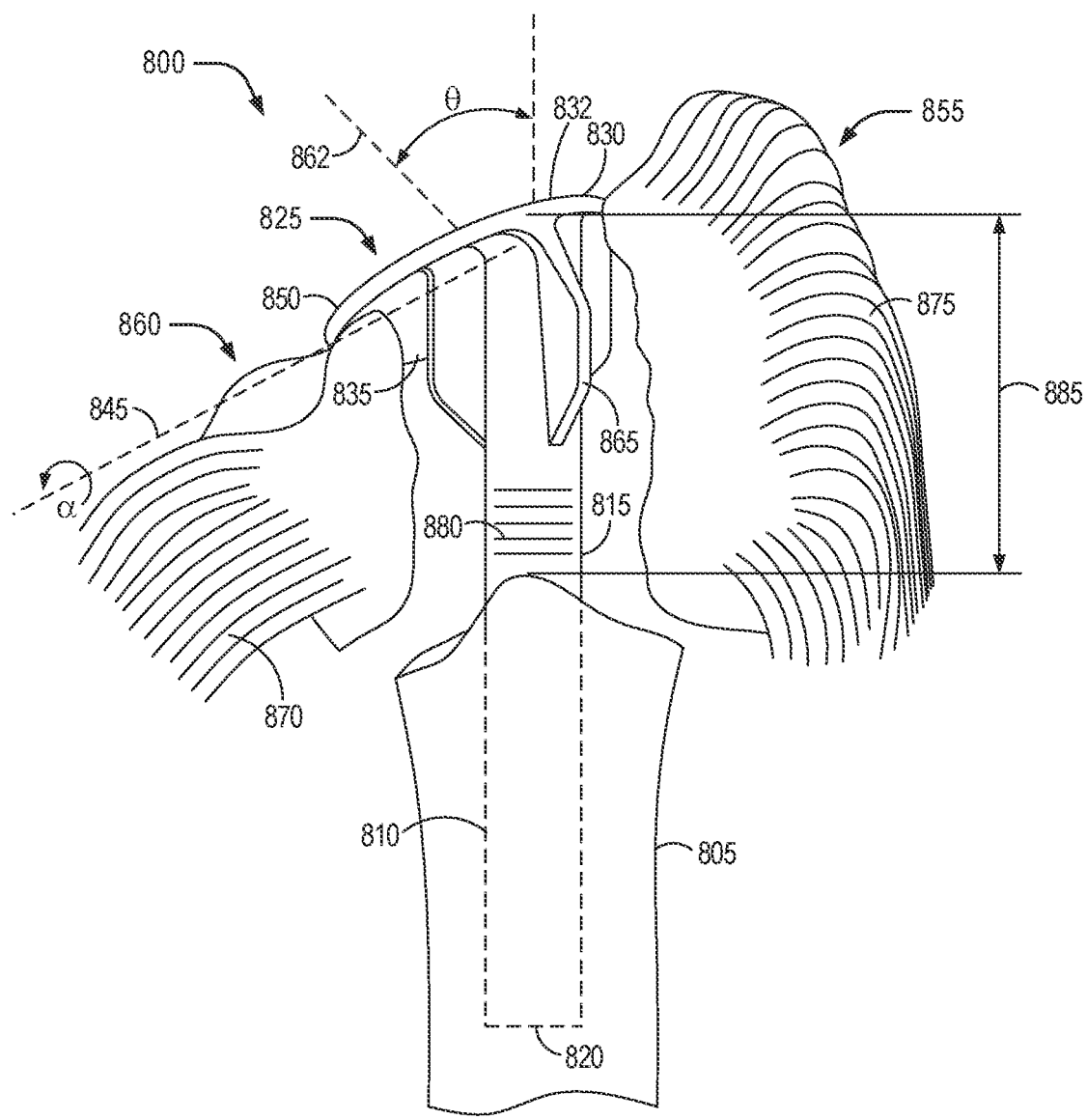
FIG. 8A illustrates a perspective view of an implant and bone fragments of a humeral bone fracture, in accordance with at least one example of the disclosure.

FIG. 8A illustrates an example of an implant 800 that is inserted into a canal within a humeral shaft 805 that includes a central shaft axis 810 during fracture repair surgery for humeral fractures including those shown in FIGS. 5A and 5B. The implant 800 can be implanted in accordance with techniques 700A and 700B discussed above. The implant 800 includes a stem portion 815 at a distal end 820. While shown as having a uniform diameter, the stem portion 815 in another example may taper. The stem portion 815 extends from the distal end 820 of the implant to adjacent a humeral head 825 at a proximal end 830.

The humeral head 825 of the implant is generally rounded and has a proximal surface 832 and distal surface 835. The proximal surface 832 in one example is generally flat and in another example, is generally spherical. The distal surface 835 in one example is generally flat and forms an angle α with a plane 845 defined by the engagement surface 850 of the bone fragments 855 of the humeral head 860 of the patient. Rotation of the humeral head 825 of the implant 800 about the plane 845 provides an inclination angle α of the implant.

The humeral head 825 of the implant 800 additionally has a central axis 862 that aligns with the glenoid. The central axis 862 forms an angle 9 with the central shaft axis 810 to define a version angle of the implant 800.

Fin elements 865 extend from the stem portion 815 adjacent the humeral head 825 of the implant for receiving the bone fragments 855 of the patient's humeral head 860. In the example of FIG. 8a, where a four-part fracture is presented, the bone fragments 855 of the humeral head 860 of the patient are a lesser tuberosity 870 and greater tuberosity 875 that engage the fin elements 865 as the lesser tuberosity and greater tuberosity 870, 875 are placed back together onto the humeral shaft 805.

In the example of FIG. 8A a mark 880 is placed on the stem portion 815 to provide a surgeon with reference regarding the height 885 of the implant 800 compared to the humeral shaft 805. The height is the distance between where the stem portion 815 is inserted into the humeral shaft 805 to the proximal end 830 of the implant 800. The mark 880 in one example is depth indicia placed on the stem portion 815. In another example a laser of the surgical system produces a laser beam or array and tracks a specific point or location on the stem. The computer system of the robotic system detects movement of the stem portion 815 and moves the array accordingly to ensure the array is always at the same distance from an end of the stem portion 815.

Figure 8B:
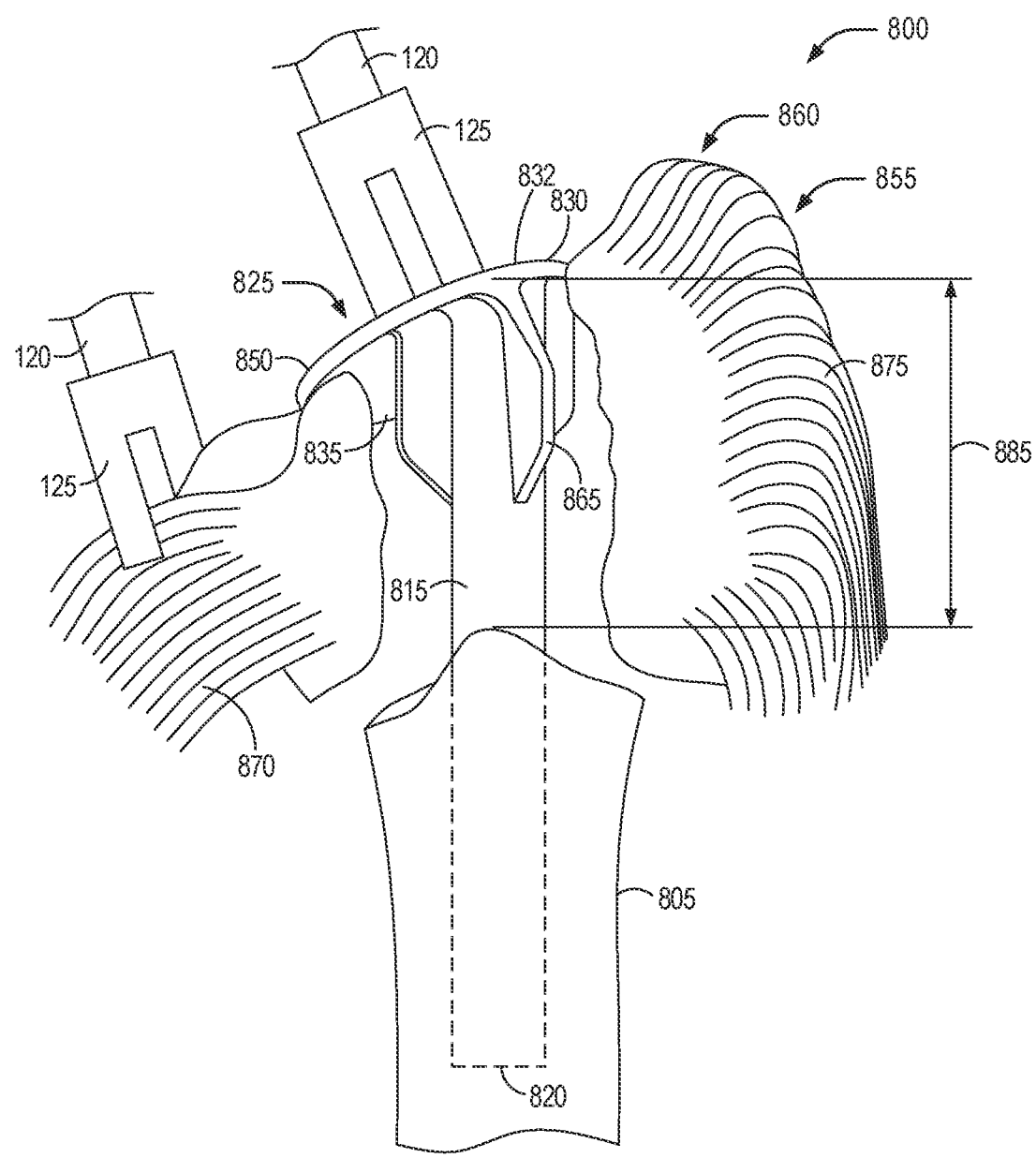
FIG. 8B illustrates a perspective view of an implant and bone fragments of a humeral bone fracture, in accordance with at least one example of the disclosure.

FIG. 8B illustrates an example of the robotic system 115 of an example surgical system 100 holding the implant 800. In this example, the surgical instrument 125 (end effector) of a robotic arm 120 is a pincer grip that grasps the humeral head 825 of the implant 800 at a desired height. Alternatively, the pincer grip or similar surgical instrument affixed to the end effector 125 can attach to an intermediate portion of the implant 800 that is designed to receive a humeral head. In this example, the end effector 125 can include an instrument adapted to attach to the implant in a manner similar to the humeral head attachment, but in a releasable manner. Upon obtaining the desired placement, including height, inclination and version angles, the pincer grip may take and place the lesser tuberosity and greater tuberosity 870, 875 in place against the fin elements 865 and stem portion 815. In one example, the pincer grip continues to hold the stem portion 815 in place as a second robotic arm 120 of the robotic system 115 also has a pincer grip that places the lesser tuberosity and greater tuberosity 870, 875 in place about the fin elements 865 and stem portion 815.

Figure 9:
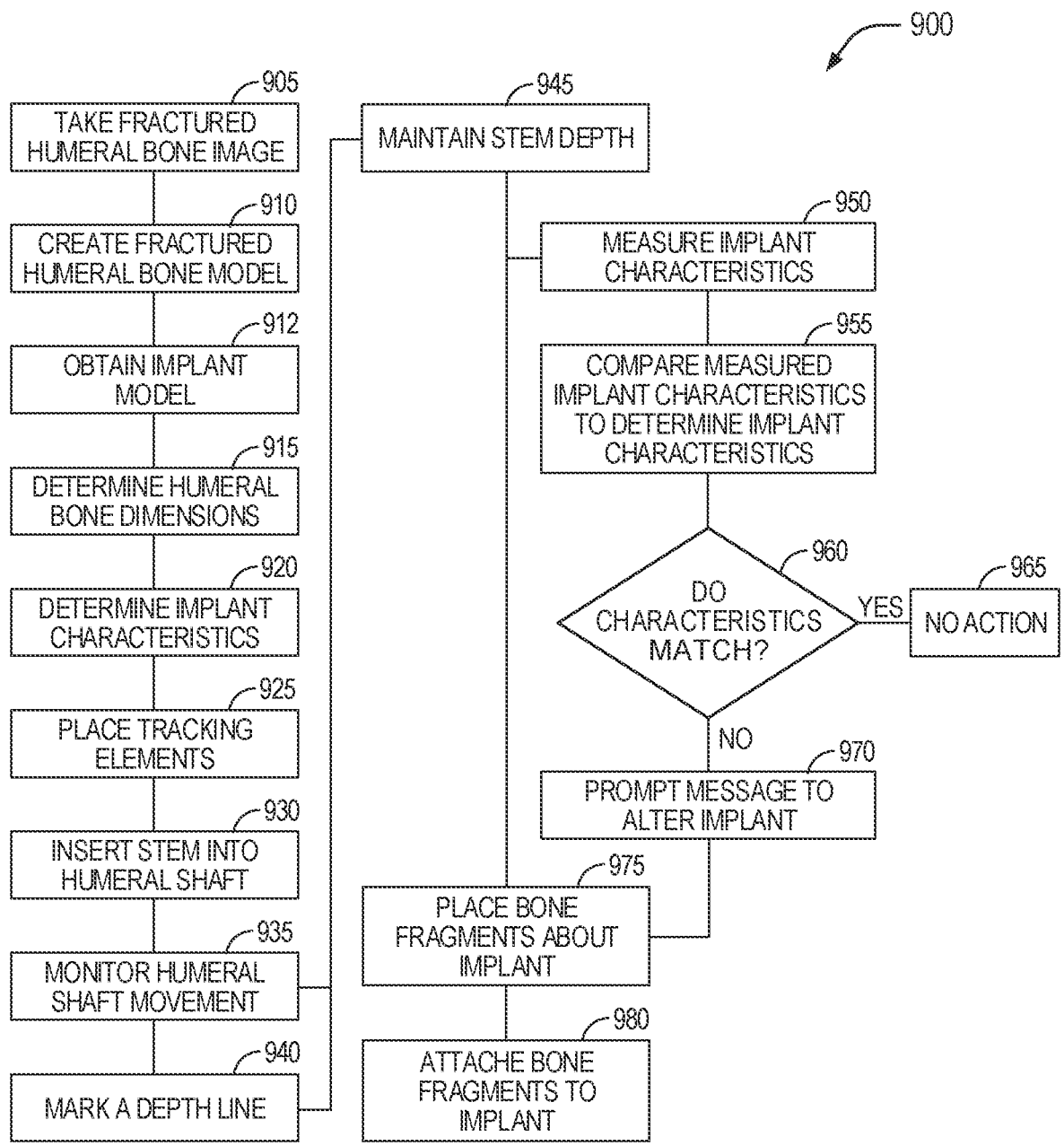
FIG. 9 illustrates a flowchart for a method of repairing a humeral bone fracture, in accordance with at least one example of the disclosure.

FIG. 9 is a flow chart illustrating a methodology of repairing a fracture 900 using an implant such as the one illustrated in the example of FIG. 8A. Technique 900 is an additional example of a robotically assisted fracture repair technique similar to techniques 700A and 700B discussed above. The technique 900 can being at 905 with the computing system 1400 accessing images of fractured humeral bone obtained in any manner as described above. At 910, the technique 900 can continue with the computing system 140 of the robotic system 115 creating a model of the fractured humeral bone. At 912, the technique 900 continues with an implant model being obtained by the computing system 140 to be used during the repair. In one example, the implant model is obtained by receiving the implant model from a remote source, such as on a memory device inserted into the computing device. In another example, the implant model is generated by the computing system 140 based on images of an implant received by the computing system 140. In one example, the obtained implant model is a three-dimension model of the implant.

At 915, the technique 900 can continue with the computing system determining the dimensions, including the size and shape of repaired humeral bone using the implant. This includes a determination regarding how bone fragments piece together about the implant and humeral shaft to reform the humeral bone with the implant. At 920, the technique 900 can continue with the computing system determining the required depth, inclination and version angles of the stem of the implant as it is inserted into a canal of the humeral shaft. In one example, the canal is reamed into the canal based on a pre-operative plan generated with respect to the models of the fractured bone and implant. At 925, the technique 900 can optionally include placement of tracking elements on the humeral shaft. Alternatively, operation 925 can involve the computing system 140 operating in cooperation with the tracking system 165 to verify placement of the tracking elements on the fractured humerus and optionally on the implant.

At 930, the technique 900 can continue with the robotic system 115 receiving the humeral shaft position from the tracking elements and operating a gripping element such as a pincer grip at the distal end of the robotic arm of the robotic system to begin insertion of the stem of the implant into the canal of the humeral shaft. Alternatively, a humeral head impactor is at the distal end of the robotic arm of the robotic system and engages the humeral head of the implant for insertion into the canal. The robotic arm of the robotic system can detach from the head of the stem and the humeral head implant mates on the same assembly that the robotic arm had been attached. At 935, the technique 900 can continue with the tracking system monitoring the humeral shaft during insertion of the stem for movement relative to the stem until the stem is at the desired depth, inclination and version angles.

Optionally, at 940, the technique 900 can continue with a depth line being marked on the stem. In an example, upon the stem of the implant reaching the desired depth, inclination and version angles, the robotic system marks with a depth line to indicate to a surgeon that the robotic arm is appropriately positioning the stem. The marking in one example is provided by a laser pointer of the robotic system that focuses a laser beam on the stem of the implant. At 945, the technique 900 can continue with the robotic system 115 maintaining location and orientation of the stem. In an example, during fracture repair, the robotic arm of the robotic system maintains the stem at the depth, inclination and version angles by physically retaining the stem. Upon detection of humeral bone movement, the robotic arm of the robotic system adjusts the implant to ensure the desired depth, inclination and version angles of the stem of the implant is provided.

At 950, the technique 900 can optionally continue with the tracking system 165 monitoring the depth, inclination and version angles of the stem of the implant. At 955, the technique 900 continues with the computer system 140 comparing the determined depth, inclination and version angles of the stem of the implant, as determined by the tracking assembly of the robotic system, with the depth, inclination and version angles of the stem of the implant determined prior to insertion to determine if the depth, inclination and version angles of the stem of the implant match.

At decision 960, the technique 900 can continue with the computing system 140 of the robotic system 115 determining if the measured implant data of 950 matches the pre-insertion determined implant data of 920. If the desired depth, inclination and version angles of the stem of the implant matches with the tracked depth, inclination and version angles of the stem of the implant, then at 965 no additional action is taken by the robotic system with regard to the depth, inclination and version angles of the stem of the implant. If at decision 960 the desired depth, inclination and version angles of the stem of the implant does not match with the tracked depth, inclination and version angles of the stem of the implant, at operation 970, the computer system 140 can present a message to the user interface device to use a different head or neck size of the implant to correct for the error.

At 975, the technique 900 can optionally continue with an auxiliary arm of the robotic system having a gripping device autonomously places the bone fragments of the humeral bone in place based on the model of the humeral bone. The bone fragments are thus matingly pieced together to reform the humerus. At 980, the bone fragments are attached to the implant. As discussed above, reattachment can be performed by the robotic system 115 or the surgeon or a combination working cooperatively. Additionally, operations 975 and 980 can be performed iteratively on each fragment positioned for reattachment. At 975, the first bone fragment can be placed around the implant followed by attachment of the first fragment at 980. The technique 900 can return to operation 975 to position the second bone fragment and continue to operation 980 to attach the second bone fragment, with the technique iterating over operations 975 and 980 until all fragments to be reattached have been addressed.

By utilizing the methodology of FIG. 9, the robotic system maintains the exact depth, inclination and version angles of the stem of the implant during repair so the surgeon can focus on other area of the repair. Additionally, the methodology allows for precise reconstruction of the bone fragments about the implant. In other methodologies, such as a revision fracture procedure when the humeral bone is desired to be replaced all the way through the elbow, the laser pointer of the robotic system projects the desired alignment of the implant components down the length of the arm of the patient.

Figure 10:
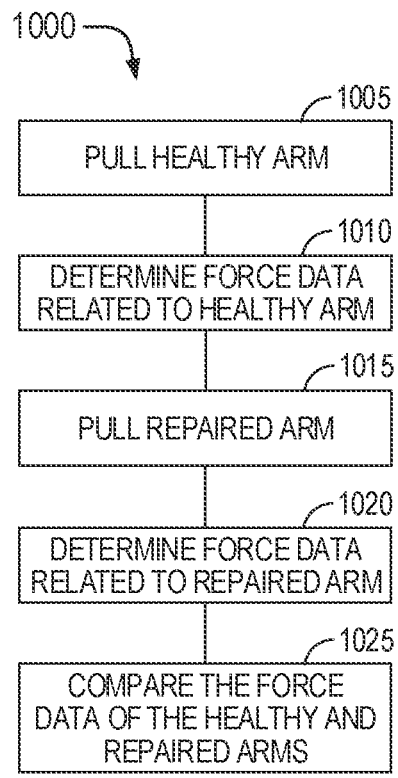
FIG. 10 illustrates a flowchart for a method of testing the range of motion of a repaired shoulder, in accordance with at least one example of the disclosure.

FIG. 10 shows yet another flow chart of a methodology, this time a methodology for post-operative range of motion 1000 is provided. At 1005 after surgery on a shoulder, a gripping device on the distal end of the robotic arm of a robotic system pulls the healthy arm of the patient that was not operated upon. At 1010, a force sensor of the robotic system determines force data related to the range of motion of the healthy arm. At 1015, the gripping device on the distal end of the robotic arm pulls the repaired arm of the patient that was operated upon with the identical force and direction as related to the healthy arm. At 1020, the force sensor of the robotic sensor determines force data related to the range of motion of the repaired arm. At 1025, the force data of the healthy arm and the force data of the repaired arm are compared to determine the range of motion between the two arms.

Figure 11:
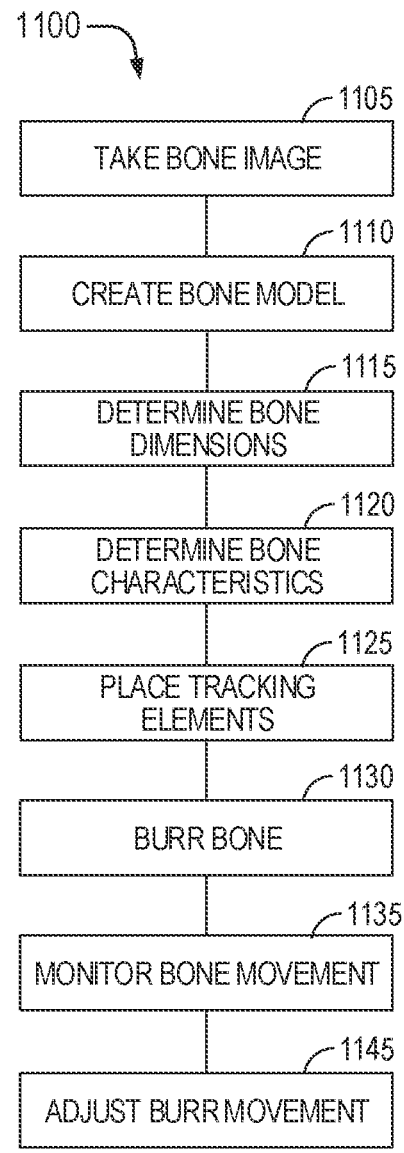
FIG. 11 illustrates a flowchart for a method of burring a bone, in accordance with at least one example of the disclosure.

Additional methodologies including using the surgical system 110 for burring processes 1100 is shown in FIG. 11. At 1105, images of the surgical area are taken in any manner as described above. At 1110, the computing system of the robotic system creates a model of surgical area that is to be burred. At 1115, the computing system determines dimensions including the end dimensions of the bone to be burred. At 1120, the computing system determines the location, angle and amount of bone to be burred. At 1125, tracking elements are placed on the bone that is to be burred.

At 1130, based on the bone position received by the robotic system from the tracking elements, burring of the bone occur. At 1135, during burring of the bone the tracking system monitors the bone for movement relative to the burr. At 1140, upon detection of movement of the bone, the robotic arm of the robotic system adjusts the burr position, angle, or depth based on the detected movement. Thus, as a result of the method, burring is adjusted based on the movement to prevent over burring.

Method/technique examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non volatile tangible computer-readable media, such as during execution or at other times. Examples of these tangible computer-readable media may include, but are not limited to, hard disks, removable magnetic disks, removable optical disks (e.g., compact disks and digital video disks), memory cards or sticks, random access memories (RAMs), read only memories (ROMs), and the like.

Figure 12:
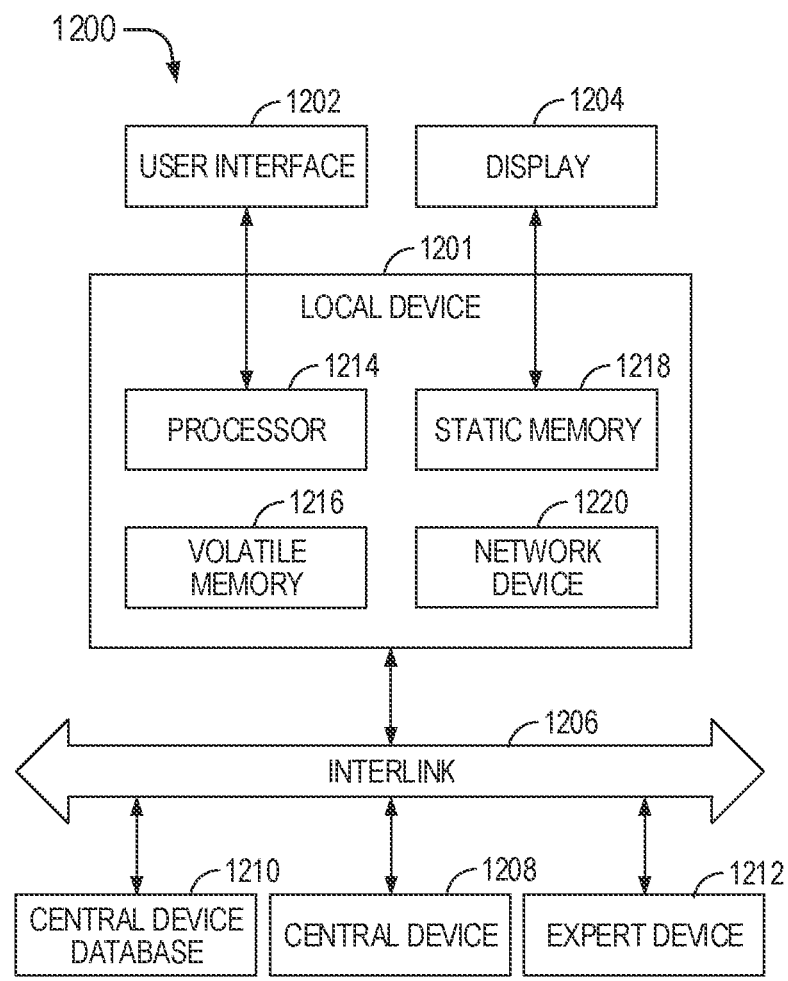
FIG. 12 illustrates a schematic diagram of a system including a machine-readable medium, in accordance with at least one example of the disclosure.

FIG. 12 illustrates a schematic showing system 1200 that is an example of the computing system 140 of the surgical system 100. The system 1200 can include local device 1201, user interface 1202, display 1204, interlink 1206, central device 1208, central device database 1210, and expert device 1212. Local device 1201 can include processor 1214, volatile memory 1216, static memory 1218, and network device 1220.

Local device 1201 can be any computing device, such as a handheld computer, for example, a smart phone, a tablet, a laptop, a desktop computer, or any other computing device including information processing and storage capabilities and communication capabilities. Local device 1201 can include processor 1214, volatile memory 1216, and static memory, which can be connected by wire or other electrical conduit within local device 1201 and can be configured to receive information, process information, output information, and store information. The information can be temporarily stored on volatile memory 1216 and can be relatively permanently stored on static memory 1218. In some examples, configurations of these components within local device 1201 can be considered machine readable medium.

The terms "machine readable medium" may include any medium that is capable of storing, encoding, or carrying instructions for execution by the device and that cause the device to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

User interface 1202 can be any input and/or output device. For example, user interface can be a monitor, keyboard, and mouse in one example. In other examples, user interface 1202 can be a touch screen display. Display 1204 can be a display for displaying output from local device 1201 and in some examples, can receive input and transfer input to local device 1201 (for example a touch screen display).

Central device 1208 can be a remote device similar in configuration to local device 1201, but located remotely from local device 1201. Central device 1208 can be configured to connect to multiple of local devices 1201, in some examples, through interlink 1206. Similarly, expert device 1212 can be a remote device similar in configuration to local device 1201, but can be operated by a user considered to be an expert. In operation of some examples, the expert user can interface with the processes and decisions of the methods discussed herein.

In some examples, user interface and display 1204 can be connected to local device 1201 through wired connections, in some examples (such as USB, for example), and through wireless connections (such as Bluetooth, for example) in other examples. In some other examples, interlink 1206 can be a local area network (LAN), wide area network (WAN), and internet protocol (TCP/IP) connections. Local device 1201 can be similarly connected to interlink 1206 (either through a wired or wireless connection). In some examples, network device 1220 can connect local device 1201 to interlink 1206. Central device 1208, central device database 1210, and expert device 1212 can be connected to interlink 1206 in a similar manner.

In operation of some examples, system 1200 can be configured to perform steps of the methods discussed herein and in some examples, may perform steps based on a program stored in volatile memory 1216 or static memory 1218, where results of the analysis are stored in either volatile memory 1216 and/or static memory 1218 can be displayed on display 1204 and/or transmitted to user interface 1202, central device 1208, central device database 1210, and/or expert device 1212. For example, system 1200 can develop a model of a shoulder by receiving an image of a patient shoulder. One of local device 1201, central device 1208, and expert device 1212 can segment the image to develop a 3D shoulder model.

Similarly, system 1200 can be configured to perform steps of each method discussed herein.

Thus, multiple methodologies for utilizing the surgical system 100 of FIG. 1 are presented. In each, a robotic system is used to improve precision and overall performance of a surgical procedure, including post procedure analysis. The improved performance is provided while still providing control to a surgeon to ensure the robotic system is performing as desired.

In certain examples, a lockable surgical arm can be utilized instead of or in addition to the robotic arm 120 to perform a segment of the functions discussed above, such as stabilizing the humerus or implant during fracture repair. In some examples, the lockable surgical arm can be used for fixed stabilization of the humerus under repair and/or stabilization of the implant in a desired location. While the lockable surgical arm, discussed in greater detail below, stabilizes the humerus and/or implant, the robotic arm 120 can function to assist in reassembly of fracture pieces. The lockable surgical discussed below provides a perfect mechanism to free up both the surgeon and the robotic arm 120 to perform more dynamic tasks. Further details on an example repositionable, lockable surgical arm system are provided in co-pending applications U.S. application Ser. No. 15/560,894, titled "Rapidly Repositionable Powered Support Arm," filed Sep. 22, 2017; and U.S. application Ser. No. 15/918,531, titled "End Effector Coupler for Surgical Arm," filed Mar. 12, 2018; both of which are hereby incorporated by reference in their entirety. The following introduces the basic components of an example lockable surgical arm and details an example surgical procedure utilizing the surgical arm in conjunction with the surgical system 100 discussed above.

FIG. 13 illustrates a perspective view of repositionable, lockable surgical arm system 1300, in accordance with at least one example of this disclosure. The lockable surgical arm system 1300 can include table 1302, arm 1304, tool (or instrument) 1305, and base unit 1306. Table 1302 can include rail 1318. Base unit 1306 can include pole 1308 and manual clamp 1310. Arm 1304 can include proximal joint 1311, actuator unit 1312, distal joint 1313, proximal arm 1314, distal arm 1315, and instrument holder 1318. Also shown in FIG. 13 are orientation indicators Proximal and Distal (shown and discussed with respect to the adjustable arm).

Base unit 1306, which can be an electrically powered actuator, can be secured to railing 1316 of surgical table 1302 using, for example, a clamp. Manual clamp 1310 of base unit 1306 can be operated to tighten base unit 1306 against railing 1316 and can also allow for adjustment of pole 1308 to set a height of arm 1304 above surgical table 1302.

Electric actuator unit 1312 of arm 1304 can be located near a proximal end of arm 1304 and can be coupled to pole 1308 at proximal joint 1311. Electric actuator 1312 can also be coupled to a proximal portion of proximal arm 1314. Proximal arm 1314 can be coupled to electric actuator 1312 via a joint or as an actuatable part of actuator 1312 in other examples. Distal arm 1315 can be coupled to a distal portion of proximal arm 1314 via distal joint 1313. Instrument holder or end effector coupler 1318 can connect instrument 1305 to the distal end of arm 1304. In some examples, a lock/unlock button can be provided on or near end effector coupler 1318.

The arms of lockable surgical arm system 1300 can comprise a serial linkage of arm segments joined by spherical and rotational joints. Each of joints 1311 and 1313 (and any other joints in other examples) can be pivotable and/or rotational joints allowing movement of connected components with one or more degrees of freedom. Joints 1311 and 1313 (and joints within actuator 1312) can be locked and unlocked using base unit 1306 and actuator 1312, which can be an electric bilateral actuator. In some examples, the joints of the arm are locked and unlocked with a fluid system.

While only proximal arm 1314 and distal arm 1315 are shown in FIG. 13, additional arm segments can be provided between actuator 1312 and end effector coupler 1318. Each additional arm segment may require one or more additional joint to form a repositionable, lockable support arm structure. Such additional arm segments can provide greater coverage and ability for the arm be positioned with more degrees of freedom in the surgical field.

In operation of some examples, the lock/unlock button can be operable by a user to initiate power locking and unlocking of arm 1304. When the lock/unlock button is not depressed arm 1304 can be in a locked state where joints 1311 and 1313 are locked such that proximal arm 1314 and distal arm 1315 cannot move relative to each other or to table 1302. When the lock/unlock button is pressed, actuator 1312 can unlock joints 1311 and 1313 such that end effector coupler 1318 can be positioned, as desired, and as guided by joints 1311 and 1313 and proximal arm 1314 and distal arm 1315. That is, end effector coupler 1318 can be moved to a desired position relative to body 50 through movement paths limited by the freedom of arm 1304 to position instrument 1305 to a desired position relative to body 50.

Figure 14A:
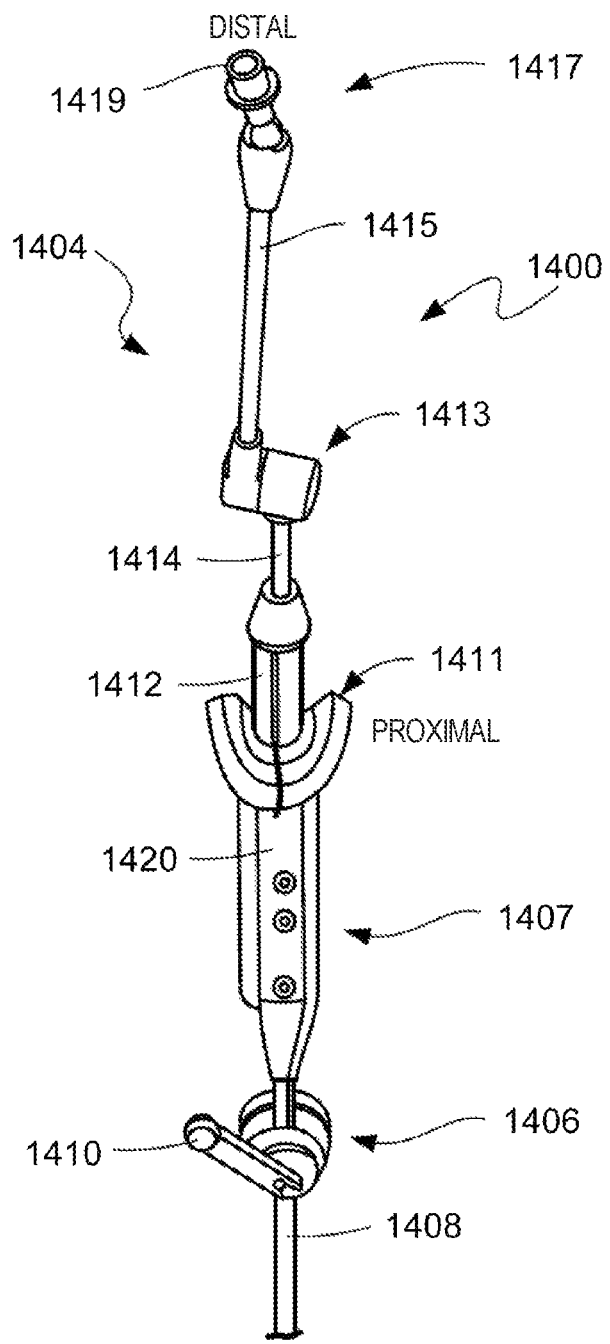
FIGS. 14A and 14B illustrate additional view of a lockable surgical support arm, in accordance with at least one example of the disclosure.
Figure 14B:
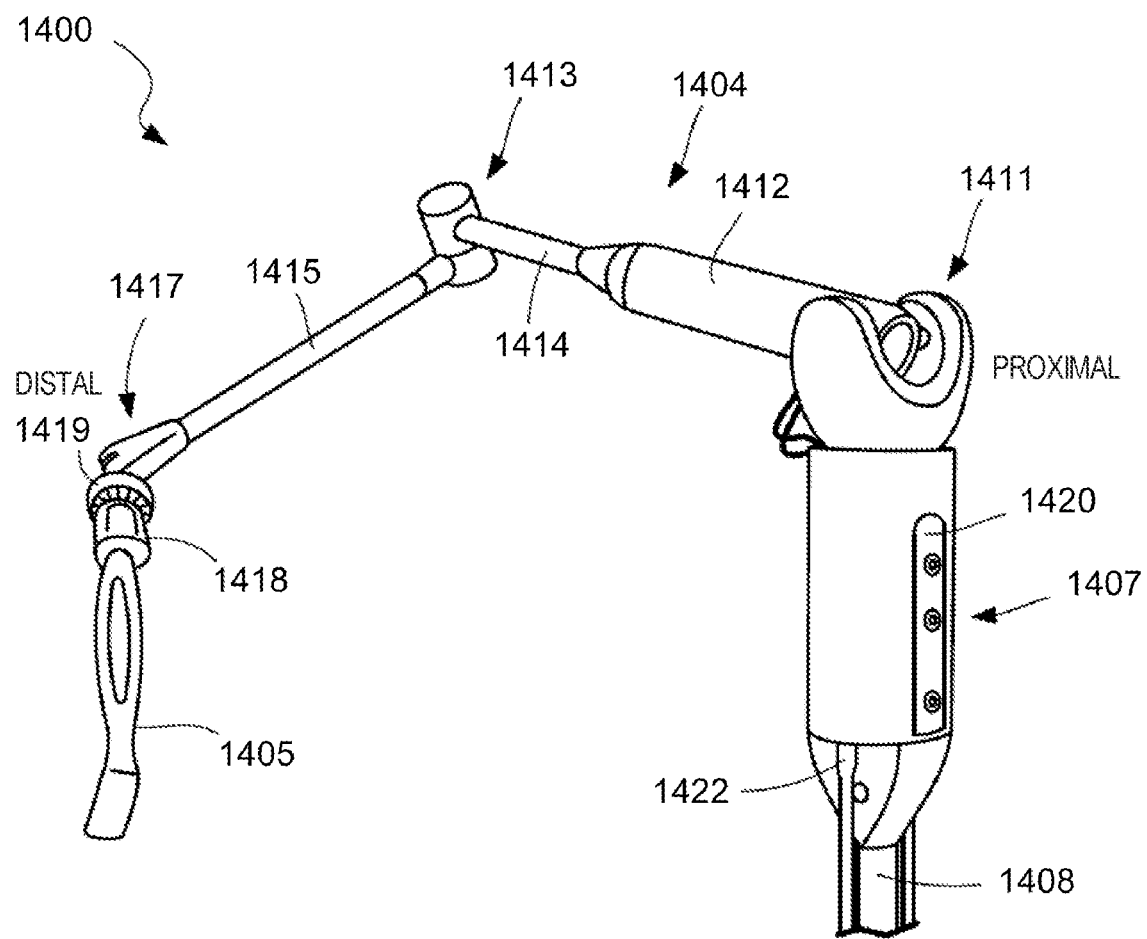

FIG. 14A illustrates a perspective view of surgical arm system 1400, in accordance with at least one example of this disclosure. FIG. 14B illustrates a perspective view of surgical arm 1400, in accordance with at least one example of this disclosure. FIGS. 14A and 14B are discussed below concurrently.

Surgical arm 1400 can include arm 1404, tool (or instrument) 1405, base unit 1406 (only shown in FIG. 14B), control device 1407, pole 1408, and manual clamp 1410. Arm 1404 can include proximal joint 1411, actuator unit 1412, distal joint 1413, proximal arm 1414, distal arm 1415, coupler joint 1417, end effector coupler 1418, arm coupler 1419. Control device 1407 can include user interface 1420 and can be connected to cable 1422. Also shown in FIG. 14 are orientation indicators Proximal and Distal.

Surgical arm 1400 can be similar to system 1300 discussed above, except that surgical arm 1400 can include different features. For example, base unit 1406 can be a manually adjustable unit, where manual clamp 1410 can be operable to adjust a position of base unit 1406 along a rail (e.g., surgical table rail) and to adjust the height of pole 1408 (and therefore arm 1404). In this example, control device 1407 can include electronic components configured to control arm 1404. For example, control device 1407 can house a controller (discussed further below) and user interface 1420, which can include one or more control inputs (such as buttons and switches) and can include audible or visual indicia. Cable 1422 can be coupleable to control device 1407 to connect a lock/unlock button to control device 1407.

Surgical arm 1400 can also include arm coupler 1419 which can be a distal coupler of arm 1404 configured to releasably secure end effector coupler 1418 to coupler joint 1417 (and therefore to arm 1404). In other examples, discussed below, end effector coupler 1418 can be fixedly secured to arm 1404.

Surgical arm 1404 can operate consistently with system 1300 described above, except that coupler joint 1417 can offer additional range of motion of the embodiment shown in FIG. 13. Further, end effector coupler 1418 can be used to quickly and easily remove and secure tools and instruments, such as tool 1405, to surgical arm 1404, as discussed in further detail below.

Figure 15A:
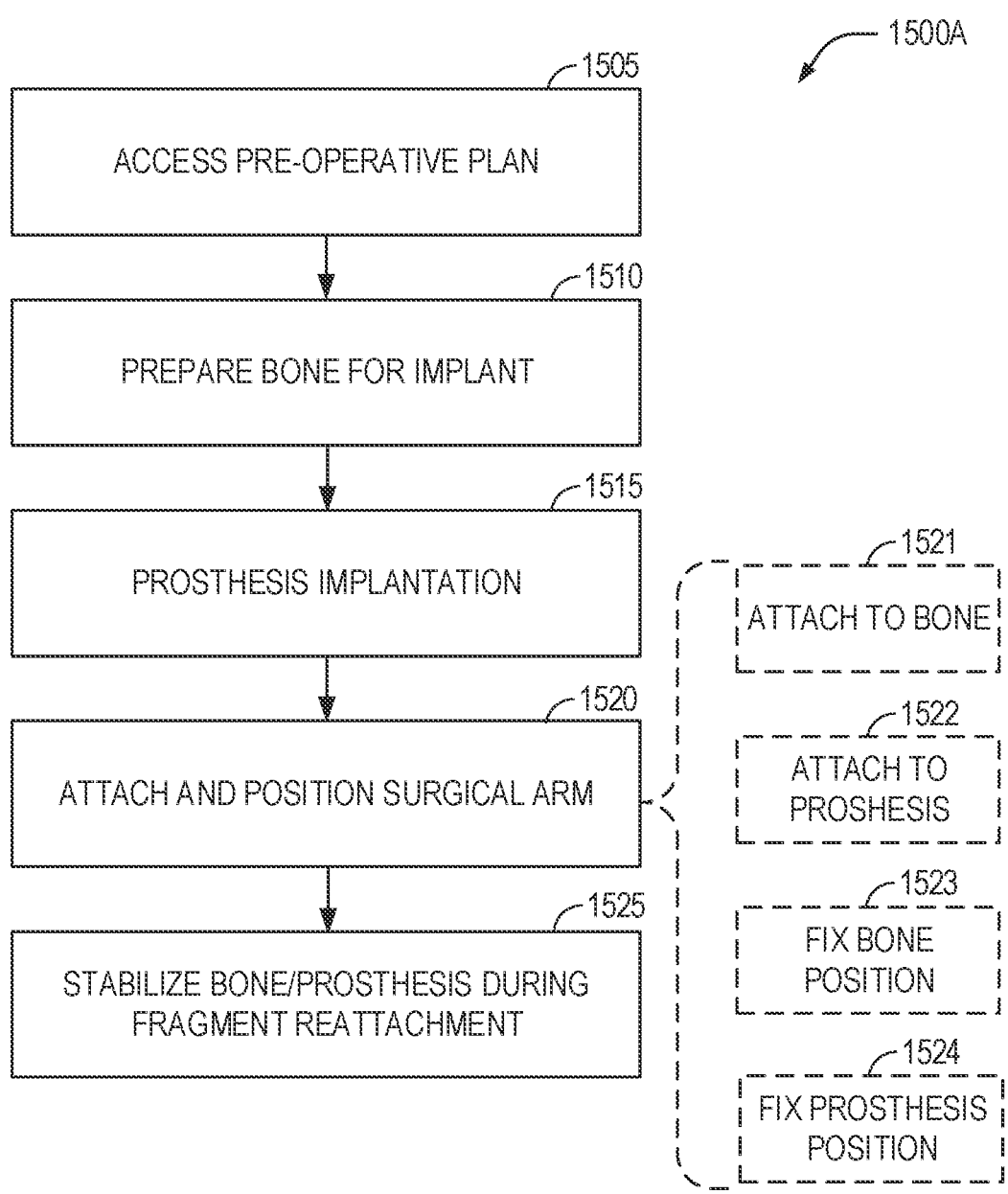
FIGS. 15A and 15B are flowcharts illustrating surgical techniques using a lockable surgical support arm, in accordance with at least one example of the disclosure.
Figure 15B:
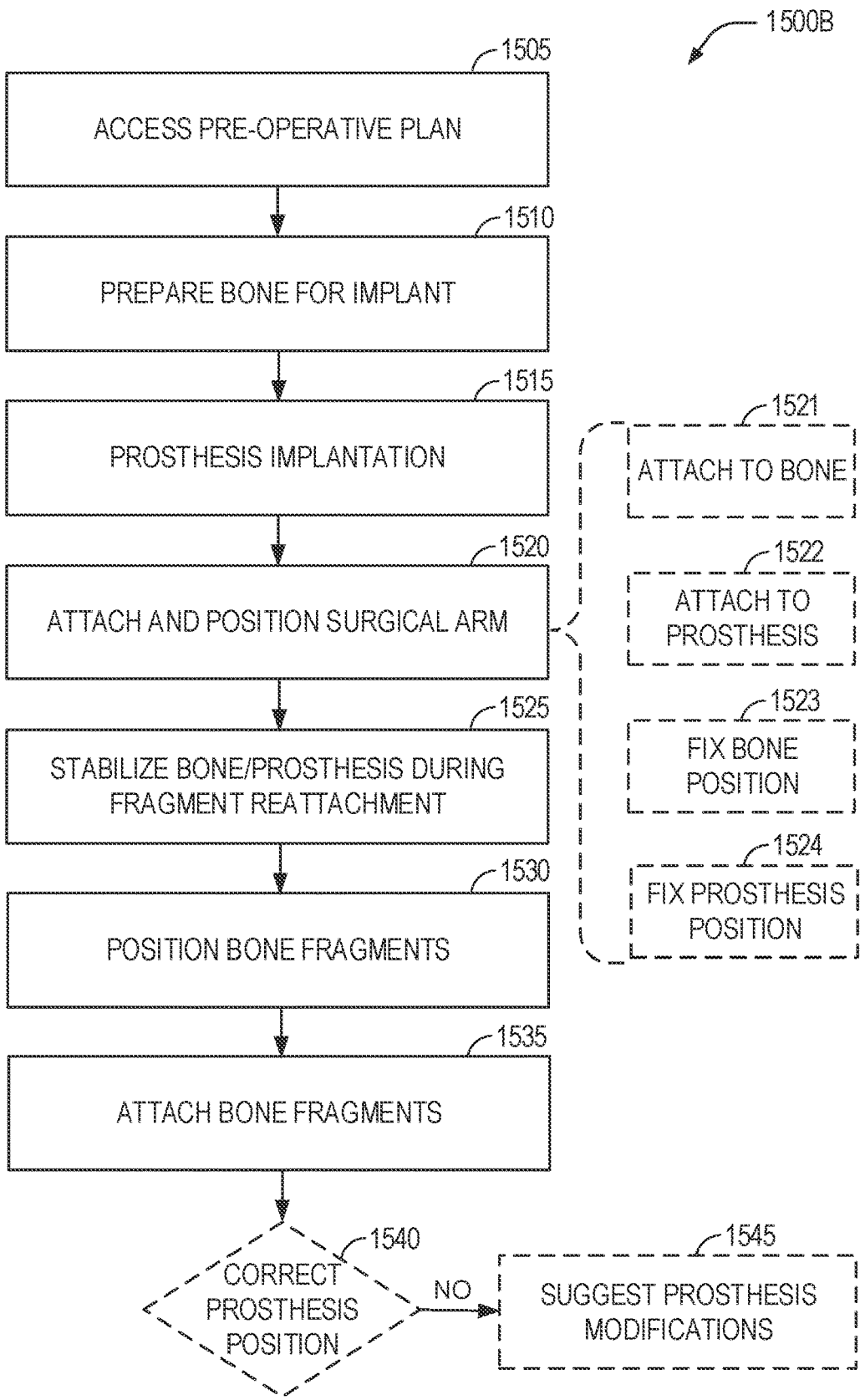

FIGS. 15A and 15B are flowcharts illustrating surgical techniques using a lockable surgical support arm, in accordance with at least one example of the disclosure. The techniques discussed in reference to these figures build on the techniques illustrated in FIGS. 7A and 7B, discussed above. In the example illustrated in FIG. 15A, the technique 1500A can include operations such as accessing a pre-operative plan at 1505; preparing a bone for an implant at 1510; implanting the prosthesis (implant) at 1515; attaching and positioning a surgical arm at 1520; stabilizing the bone and/or prosthesis during fragment reattachment at 1525. Optionally, the operation for attaching and positioning the surgical arm at 1520 can include attaching an end effector of the surgical arm to a bone at 1521, attaching an end effector of the surgical arm to a prosthesis at 1522, fixing the bone position at 1523 and fixing the prosthesis position at 1524.

The technique 1500A can begin at 1505 with the computing system 140 executing instructions to access a pre-operative plan, such as the pre-operative plan generated with technique 600 (discussed above). At 1510, the technique 1500A can continue with operations necessary to prepare the bone for implantation of the prosthesis in accordance with the pre-operative plan. The operation 1510 can include either manual preparation of the bone by the surgeon in accordance with the preoperative plan, or preparation of the bone using a robotic arm, such as robotic arm 120. In an example utilizing the robotic arm 120, the operation 1510 can include a number of operations discussed in reference to FIG. 7A, including initializing the robotic system 115 at 710, reaming to create a cavity in the bone, such as the humeral shaft, using the robotic arm 120 at 715.

At 1515, the technique 1500A can continue with the robotic arm 120 implanting the prosthesis in accordance with the pre-operative plan, as discussed in detail in reference to operation 720. In other examples, the surgeon can manually implant the prosthesis without assistance from the robotic arm 120. In yet other examples, the surgeon and robotic arm 120 may operate cooperatively to perform the implantation, such as with the surgeon guiding the robotic arm 120. Prosthesis implantation may include the use of bone cement to hold the prosthesis in the bone. In procedures including the use of bone cement, securing the prosthesis relative to the bone for a period of time can be important to allow the bone cement to cure.

Once the prosthesis is in place in the bone, such as within the reamed out cavity in the humerus, the technique 1500A can continue at 1520 using one or more surgical support arms, such as surgical arm 1400, to maintain position of the bone and/or prosthesis during subsequent operations. In an example, a surgical arm 1400 can include an end effector that couples to a portion of the bone, such as via a cuff or padded clamping mechanism. At 1521, the technique 1500A can optionally continue with the surgical arm 1400 being attached to the bone. Once attached to the bone, the technique 1500A can continue at 1523 with the surgical arm 1400 being adjusted to position the bone as desired and then locked into that position fixing the bone in the desired orientation at 1523. In examples where a second surgical arm is used to control the prosthesis, the technique 1500A can optionally continue with the second surgical arm being attached to the prosthesis at 1522. In this example, the second surgical arm can include an end effector adapted to easily couple to a portion of the prosthesis, such as the humeral head or an upper segment of the humeral stem. Once the second surgical arm is coupled to the prosthesis, the technique 1500A can optionally continue at 1524 with the second surgical arm being adjusted to position the prosthesis in the desired orientation, and then the second surgical arm can be locked to maintain the desired orientation of the prosthesis. The technique 1500A can complete at 1525 utilizing one or more surgical support arms, such as surgical arm 1400, to stabilize the bone and/or the prosthesis. In an example utilizing two surgical support arms, the arms can maintain positioning of both the bone and the prosthesis, which can then allow a surgeon or a robotic arm perform additional tasks. In some examples, a single surgical support arm can be used with the robotic arm 120 operating to stabilize either the bone or the prosthesis while the surgeon performs additional tasks, such as fracture repair or further securing the prosthesis with bone cement. In some examples, one or more surgical support arms can be used to secure the prosthesis to allow bone cement time to cure, at least initially.

FIG. 15B illustrates a technique 1500B where one or more surgical support arms are utilized to stabilize bone and/or prosthesis while a surgeon or robotic arm repairs a fracture. As illustrated in FIG. 4, fracture repair of a broken shoulder can be complicated and require positioning and reattachment of multiple bone fragments, while maintaining proper prosthesis positioning. As discussed in reference to FIG. 15A, one or more surgical support arms can be used to stabilize both the bone and the prosthesis, through operations 1505 through 1525. The technique 1500B can pick up at operation 1530 with the robotic arm or the surgeon positioning bone fragments around the prosthesis, while the bone and prosthesis are stabilized. At 1535, the technique 1500B can continue with the surgeon (or in some cases the robotic arm) suturing or otherwise attaching the bone fragments to each other, the intact portion of the bone, and/or the prosthesis. In some examples, the robotic arm can be used to position the bone fragment, while the surgeon works to secure it in place. Optionally, the technique 1500B can continue at 1540 with the position of the prosthesis being verified after reattachment of all bone fragments. Position verification can be done through landmarks on the prosthesis or through use of optical tracking markers on the prosthesis or the surgical support arm, among other methods. In certain examples, the robotic arm 140 can be used to verify prosthesis positioning through contact with known positions on the prosthesis can bone landmarks. At 1545, the technique 1500B can optionally continue with the computer system 140 calculating suggested modifications to prosthesis positioning after receiving input on the actual location of the prosthesis relative to the bone. The technique 1500B can iterate through operations 1540 and 1545 as necessary to achieve optimal prosthesis positioning.

Shoulder joint arthroplasty requires careful attention to preservation of soft tissue balance to maintain or regain proper range of motion in the joint after implantation of a prosthesis. The shoulder is a complex joint that requires ligaments and muscle to maintain proper stability through a wide range of motion desired from a healthy joint. Accordingly, during shoulder arthroplasty procedures it is beneficial to analyze soft tissue conditions and select prosthetic implants that are properly sized to obtain a desired amount of tension within the repaired joint. If the soft tissues are loose the joint will have poor stability. If the tissues are too tight range of motion is be inhibited.

The robotic system 100 discussed above can be utilized to assist in assessing soft tissue conditions with the joint under repair and the computing system 140 can collect and analyze joint data to suggest an optimal prosthesis for the observed conditions. In general, the robotic system 100 can be utilized to induce a known amount of tension into the joint, and collect data regarding the reaction of the joint to the applied tension. The collected data can include position and orientation of the bone associated with the joint, which can then be utilized to select a proper prosthesis and guide additional surgical operations if necessary. Additional surgical operations can include soft tissue releases or related repairs.

Figure 16:
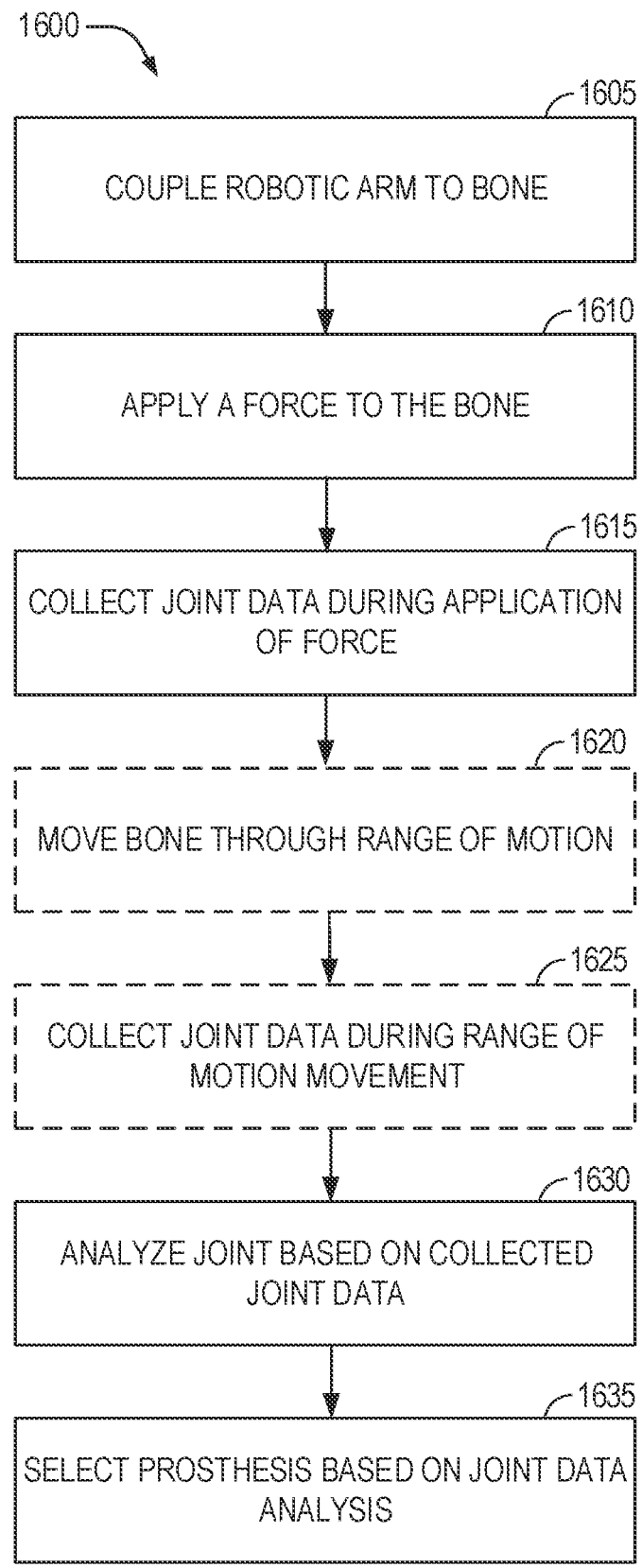
FIG. 16 is a flowchart illustrating a surgical technique for conducting joint analysis with assistance from a robotic arm, in accordance with at least one example of the disclosure.

FIG. 16 is a flowchart illustrating a surgical technique for conducting joint analysis with assistance from a robotic arm, in accordance with at least one example of the disclosure. In this example, the technique 1600 can include operations such as: coupling a robotic arm to a bone at 1605; applying a force to the bone at 1610; collecting joint data at 1615; optionally moving bone through a range of motion at 1620; optionally collecting additional joint data at 1625; analyzing joint based on collected data at 1630; and selecting a prosthesis at 1635. The technique 1600 can begin at 1605 with the robotic arm 120 being coupled to a patient's bone, such as a humerus. The robotic arm 120 can include an end effector that connects to an arm cuff or similar restrain to enable the robotic arm 120 to control the positioning of the humerus. The end effector can include a multiple degree of freedom coupling to enable the humerus to move in certain directions relatively freely during data collection, which enable collection of data related to how the different soft tissues in the shoulder joint react to the forces applied by the robotic arm.

At 1610, the technique 1600 can continue with the robotic arm 120 applying a force to the humerus, in this example. The force applied by the robotic arm 120 can be applied along a vector calculated to separate the humerus from the glenoid in a known manner that attempts to equally stress soft tissues within the shoulder joint. At 615, the technique 1600 can continue with the computing system 140 collecting joint data during application of the force at 1610. The joint data can include position of the humerus relative to the glenoid, gap distances in the shoulder joint, and orientation of the humerus. The orientation of the humerus can indicate relative tensions in the different soft tissues in the shoulder joint.

At 1620, the technique 1600 can optionally continue with a range of motion test. In some examples, the robotic arm 120 can be programmed to move the humerus through a range of motion. In other examples, the surgeon can disconnect the robotic arm 120 and move the humerus through the range of motion manually. In either scenario, the technique 1600 can optionally continue at 1625 with the computer system 140 collecting joint data throughout the range of motion test. In an example, at least some of the joint data is collected through an optical tracking system tracking optical tracking markers, such as optical tracking system 165 tracking markers 170.

At 1630, the technique 1600 can continue with the computer system 140 analyzing the joint data collected in operations 1615 and 1625. The analyzed data can then be used at 1635 by the computer system 140 to select a prosthesis for use in repair of the shoulder based on the joint data. For example, the gap size or average gap size over the range of motion may be used to assist in size selection of a prosthesis.

VARIOUS NOTES & EXAMPLES

Example 1 is a method of inserting a humeral implant into a humerus of a patient. The method includes receiving selection of a virtual humeral implant including humeral implant dimensions; receiving a patient position from one or more position sensors secured to the patient; and adjusting a position of the humeral implant relative to the humerus based on at least one of the patient position, and the humeral implant dimensions.

In Example 2, the subject matter of Example 1 optionally includes displaying on a user interface device a graphic representation of the humeral implant dimensions.

In Example 3, the subject matter of any one or more of Examples 1-2 optionally include wherein the humeral implant dimensions includes one or more of height, inclination, or version of the humeral implant.

In Example 4, the subject matter of any one or more of Examples 1-3 optionally include reaming the humerus to create a humeral canal based on at least one of the patient position, and the humeral implant dimensions.

In Example 5, the subject matter of Example 4 optionally includes inserting the implant into the humeral canal of the humerus with a robotic system based on at least one of the patient position and the humeral implant dimensions.

In Example 6, the subject matter of Example 5 optionally includes receiving an image of a patient shoulder comprising a humerus; developing a three-dimensional (3D) shoulder model.

In Example 7, the subject matter of Example 6 optionally includes D shoulder model.

In Example 8, the subject matter of Example 7 optionally includes obtaining force data with a force sensor of the robotic system to determine a post-surgery range of motion of the patient shoulder.

In Example 9, the subject matter of any one or more of Examples 1-8 optionally include securing the humeral implant to the humerus while implant position is adjusted automatically based on at least one of the patient position, the implant position, or the humeral implant dimensions.

In Example 10, the subject matter of Example 9 optionally includes wherein the implant position is adjusted by a robotic arm.

In Example 11, the subject matter of any one or more of Examples 9-10 optionally include wherein the implant position is adjusted automatically based on an image of a healthy shoulder of the patient.

In Example 12, the subject matter of any one or more of Examples 1-11 optionally include receiving an image of a patient shoulder comprising the humerus, wherein the image of the patient shoulder is received from at least one of computed tomography (CT) scan, magnetic resonance imaging (MRI), ultrasound, two-dimensional x-ray, or three-dimensional x-ray.

In Example 13, the subject matter of Example 12 optionally includes creating a three-dimensional model of a shoulder joint of a patient and a three-dimensional model of the implant.

In Example 14, the subject matter of Example 13 optionally includes wherein the image includes a plurality of bone fragments of the patient.

In Example 15, the subject matter of Example 14 optionally includes virtually reassembling the plurality of bone fragments.

In Example 16, the subject matter of any one or more of Examples 1 optionally include wherein the humeral implant is a humeral head implant that includes an interface for an optical tracking assembly.

In Example 17, the subject matter of Example 16 optionally includes providing an expected humeral head position; determining a humeral head position with the optical tracking assembly; comparing the humeral head position to the expected humeral head position to determine differences in the expected humeral head position and humeral head position.

In Example 18, the subject matter of Example 17 optionally includes wherein the expected humeral head position is determined by optical navigation.

In Example 19, the subject matter of any one or more of Examples 17-18 optionally include wherein the expected humeral head position and humeral head position are the same.

In Example 20, the subject matter of any one or more of Examples 17-19 optionally include wherein the expected humeral head position and the humeral head position are different.

In Example 21, the subject matter of Example 20 optionally includes automatically prompting a message on a user interface device to change a head size or neck size of the humeral head implant.

In Example 22, the subject matter of any one or more of Examples 1-21 optionally include the robotic system comprises a first robotic arm that inserts the implant into the humeral canal of the humerus and a second robotic arm that holds the humerus during insertion of the implant into the humeral canal.

In Example 23, the subject matter of any one or more of Examples 1-22 optionally include aligning the humeral implant in the humerus with a laser pointer of a robotic system.

Example 24 is a method for guiding a surgical instrument, the method comprising: receiving an image of a glenoid in a three-dimensional space; tracking movement in glenoid position of a patient in the three-dimensional space with a computer-operated tracking system; placing a guide pin within the glenoid with the surgical instrument based on the image of the glenoid and tracked movement in the glenoid position.

In Example 25, the subject matter of Example 24 optionally includes wherein the image is at least one of computed tomography (CT) scan, magnetic resonance imaging (MRI), ultrasound, two-dimensional x-ray, or three-dimensional x-ray.

In Example 26, the subject matter of any one or more of Examples 24-25 optionally include tracking a humerus bone position within the three-dimensional space using the computer-operated tracking system; and placing the guide pin within the glenoid further based on the humerus bone position.

In Example 27, the subject matter of any one or more of Examples 24-26 optionally include wherein a robotic system places the guide pin within the glenoid.

In Example 28, the subject matter of Example 27 optionally includes wherein the robotic system comprises the computer-operated tracking system and a robotic arm operated by the computer-operated tracking system.

In Example 29, the subject matter of Example 28 optionally includes wherein the robotic arm has a pincer grip to hold the guide pin.

In Example 30, the subject matter of any one or more of Examples 28-29 optionally include wherein the computer-operated tracking system actuates the robotic arm to position the guide pin.

In Example 31, the subject matter of any one or more of Examples 24-30 optionally include wherein the computer-operated tracking system comprises an optical tracking assembly that receives input from at least one tracking element secured to the glenoid.

Example 32 is a method for preparing a humeral bone for an implant, the method comprising: tracking a humeral bone position within a three-dimensional space using a computer-operated tracking system of a robotic system; receiving an image of the humeral bone; reaming a canal within the humeral bone with a surgical instrument of a robotic system; during reaming, tracking movement in the humeral bone position; and adjusting position of the surgical instrument based on the movement in humeral bone position.

In Example 33, the subject matter of Example 32 optionally includes wherein the surgical instrument is an effector of a robot arm of the robotic system.

In Example 34, the subject matter of Example 33 optionally includes wherein the effector is a reamer.

In Example 35, the subject matter of any one or more of Examples 32-34 optionally include wherein the robotic system comprises a first robotic arm having a reamer for reaming the canal in the humeral bone and a second arm having a gripping device to hold the humeral bone.

Example 36 is a surgical system comprising: a robotic system comprising a computer-operated tracking system comprising at least one tracking element that obtains position data related to a bone of a patient and sends the position data to the robotic system; and the robotic system comprising a robotic arm that moves in relation to the bone based on the position data related to the bone obtained by the at least one tracking element.

In Example 37, the subject matter of Example 36 optionally includes wherein the robotic arm includes a surgical instrument that comprises a burring device for removing bone.

In Example 38, the subject matter of any one or more of Examples 36-37 optionally include wherein the computer-operated tracking system has an optical navigation assembly.

In Example 39, the subject matter of any one or more of Examples 36-38 optionally include wherein the robotic system further comprises a user interface device to present a graphic representation of an implant being inserted into the bone.

In Example 40, the subject matter of any one or more of Examples 36-39 optionally include wherein the robotic system receives an image of a patient shoulder and forms a model of the patient shoulder.

In Example 41, the subject matter of Example 40 optionally includes wherein the image of the patient shoulder is received from at least one of computed tomography (CT) scan, magnetic resonance imaging (MRI), ultrasound, two-dimensional x-ray, or three-dimensional x-ray.

In Example 42, the subject matter of any one or more of Examples 36-41 optionally include wherein the robotic system further comprises a force sensor for receiving force data related to the bone.

In Example 43, the subject matter of any one or more of Examples 36-42 optionally include an implant releasably secured by an arm of the robotic system for placement in the bone.

In Example 44, the subject matter of Example 43 optionally includes wherein the implant is a humeral head implant that includes an interface for the computer-operated tracking system.

In Example 45, the subject matter of Example 44 optionally includes wherein the computer-operated tracking system has an optical tracking assembly.

In Example 46, the subject matter of any one or more of Examples 36-45 optionally include wherein the robotic system further comprises a first robotic arm that inserts an implant into the bone and a second robotic arm that holds the bone during insertion of the implant.

In Example 47, the subject matter of any one or more of Examples 36-46 optionally include wherein the robotic system further comprises a laser pointer for aligning an implant in the bone.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A robotic system for assisting with insertion of a humeral implant into a humerus of a patient, the robotic system comprising:
   a robot manipulator including an end effector adapted to position the humeral implant;
   a computing system comprising a processor, a memory device, and a display device, the memory device including instructions that, when executed by the processor, cause the computing system to perform operations including:
   creating a three-dimensional (3D) model of a shoulder joint of the patient based on an image of the shoulder joint and a three-dimensional model of a virtual humeral implant, wherein the image includes a plurality of bone fragments of the patient;
   receiving signals representative of a patient position from one or more position sensors secured to the patient; and
   sending adjustment signals to the robotic manipulator to position the humeral implant relative to the humerus based on at least one of the patient position, dimensions of the humeral implant, and the 3D model.

2. The robotic system of claim 1, wherein the memory device further includes instructions that when executed cause the computing system to perform operations including:
displaying on the display device a graphic representation of the humeral implant dimensions.

3. The robotic system of claim 2, wherein the humeral implant dimensions include one or more of height, inclination, and version of the humeral implant.

4. The robotic system of claim 1, wherein the memory device further includes instructions that when executed cause the computing system to perform operations including:
sending signals to the robotic manipulator to ream the humerus to create a humeral canal based on at least one of the patient position and the humeral implant dimensions.

5. The robotic system of claim 4, wherein the memory device further includes instructions that when executed cause the computing system to perform operations including:
sending signals to the robotic manipulator to insert the implant into the humeral canal of the humerus with the robotic manipulator based on at least one of the patient position and the humeral implant dimensions.

6. The robotic system of claim 1, wherein the memory device further includes instructions that when executed cause the computing system to perform operations including:
sending control signals to the robotic manipulator to control placing, matingly, at least a portion of the plurality of bone fragments together based on the 3D shoulder model.

7. The robotic system of claim 6, wherein the memory device further includes instructions that when executed cause the computing system to perform operations including:
obtaining force data with a force sensor disposed on the robotic manipulator to determine a post-surgery range of motion of the patient shoulder.

8. The robotic system of claim 1, wherein the memory device further includes instructions that when executed cause the computing system to perform operations including:
sending control signals to the robotic manipulator to secure the humeral implant to the humerus while implant position is adjusted automatically based on at least one of the patient position, the implant position, or the humeral implant dimensions.

9. The robotic system of claim 8, wherein the implant position is adjusted by a robotic arm.

10. The robotic system of claim 8, wherein sending control signals to secure the humeral implant include adjusting, automatically, the implant position based on an image of a healthy shoulder of the patient.

11. The robotic system of claim 1, wherein the memory device further includes instructions that when executed cause the computing system to perform operations including: virtually reassembling the plurality of bone fragments within the computing system based on the 3D shoulder model.

12. The robotic system of claim 1, wherein the humeral implant is a humeral head implant that includes an interface for an optical tracking assembly; and
wherein the memory device further includes instructions that when executed cause the computing system to perform operations including:
providing an expected humeral head position;
determining a humeral head position with the optical tracking assembly; and
comparing the humeral head position to the expected humeral head position to determine differences in the expected humeral head position and humeral head position.

13. The robotic system of claim 12, wherein the expected humeral head position is determined by optical navigation.

14. The robotic system of claim 12, wherein the memory device further includes instructions that when executed cause the computing system to perform operations including: automatically prompting a message on the display device to change a head size or neck size of the humeral head implant.

15. The robotic system of claim 12, wherein the robotic manipulator comprises a first robotic arm that inserts the implant into the humeral canal of the humerus and a second robotic arm that holds the humerus during insertion of the implant into the humeral canal.

16. A computer-readable medium comprising instructions that, when executed by a processor, cause a computing system coupled to a robotic manipulator to perform operations comprising:
receiving an image of a patient shoulder comprising a humerus;
developing a three-dimensional (3D) shoulder model, the 3D shoulder model including bone fragments;
receiving a patient position from one or more position sensors secured to the patient; and
adjusting, using the robotic manipulator, a position of a humeral implant relative to the humerus based on at least one of the patient position and the 3D shoulder model; and
placing, matingly, the bone fragments together with the robotic manipulator based on the 3D shoulder model.

17. The computer-readable medium of claim 16, further comprising instructions to cause the computing system to perform operations comprising:
reaming the humerus to create a humeral canal based on at least one of the patient position and the humeral implant dimensions.

18. The computer-readable medium of claim 17, further comprising instructions to cause the computing system to perform operations comprising:
inserting the implant into the humeral canal of the humerus with the robotic manipulator based on at least one of the patient position and the humeral implant dimensions.

* * * * *